(12) United States Patent
Steele et al.

(10) Patent No.: US 9,599,529 B1
(45) Date of Patent: *Mar. 21, 2017

(54) SYSTEMS AND METHODS FOR LIKELIHOOD-BASED MAPPING OF AREAS SURVEYED FOR GAS LEAKS USING MOBILE SURVEY EQUIPMENT

(71) Applicant: Picarro Inc., Santa Clara, CA (US)

(72) Inventors: David Steele, San Francisco, CA (US); Sze M. Tan, Sunnyvale, CA (US); Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 487 days.

This patent is subject to a terminal disclaimer.

(21) Appl. No.: 14/139,388

(22) Filed: Dec. 23, 2013

Related U.S. Application Data

(60) Provisional application No. 61/745,562, filed on Dec. 22, 2012.

(51) Int. Cl.
  *G01N 31/00* (2006.01)
  *G01M 3/04* (2006.01)
(52) U.S. Cl.
  CPC .................... *G01M 3/04* (2013.01)
(58) Field of Classification Search
  CPC .................. G01N 15/02; G01N 15/06; G01N 2015/0046; G01N 2015/1486;
  (Continued)

(56) References Cited

U.S. PATENT DOCUMENTS

| 4,690,689 A | 9/1987 | Malcosky et al. |
| 5,191,341 A | 3/1993 | Gouard et al. |

(Continued)

FOREIGN PATENT DOCUMENTS

CA   2339865 A1   7/2002

OTHER PUBLICATIONS

Gifford, Frank, "Statistical Properties of a Fluctuating Plume Dispersion Model," p. 117-137, U.S. Weather Bureau Office, Oak Ridge, Tennessee. 1959; the year of publication is sufficiently earlier than the effective U.S. filing date and any foreign priority date so that the particular month of publication is not issue.

(Continued)

*Primary Examiner* — Roy Y Yi
(74) *Attorney, Agent, or Firm* — Law Office of Andrei D Popovici, PC

(57) ABSTRACT

In some embodiments, vehicle-based natural gas leak detection methods are used to generate 2-D spatial distributions (heat maps) of gas emission source probabilities and surveyed area locations using measured gas concentrations and associated geospatial (e.g. GPS) locations, wind direction and wind speed, and atmospheric condition data. Bayesian updates are used to incorporate the results of one or more measurement runs into computed spatial distributions. Operating in gas-emission plume space rather than raw concentration data space allows reducing the computational complexity of updating gas emission source probability heat maps. Gas pipeline location data and other external data may be used to determine the heat map data.

20 Claims, 22 Drawing Sheets

(58) Field of Classification Search
CPC .. G01N 21/3504; G01N 33/004; G01N 19/10; G01N 1/26; G01N 2201/06113; G01N 2291/0215; G01N 29/02; G01N 33/0009; G01N 33/0057; G01N 33/00
See application file for complete search history.

(56) References Cited

U.S. PATENT DOCUMENTS

| | | | |
|---|---|---|---|
| 5,390,530 | A | 2/1995 | Hosonuma et al. |
| 5,946,095 | A | 8/1999 | Henningsen et al. |
| 6,532,801 | B1 | 3/2003 | Shan et al. |
| 6,664,533 | B1 | 12/2003 | van der Laan et al. |
| 6,815,687 | B1 | 11/2004 | Branch-Sullivan et al. |
| 6,822,742 | B1 * | 11/2004 | Kalayeh ................. G01N 21/31 250/338.1 |
| 6,995,846 | B2 | 2/2006 | Kalayeh et al. |
| 7,352,463 | B2 | 4/2008 | Bounaix |
| 7,486,399 | B1 | 2/2009 | Reichardt et al. |
| 7,934,412 | B2 | 5/2011 | Prince |
| 8,000,936 | B2 | 8/2011 | Davis |
| 8,081,112 | B2 | 12/2011 | Tucker et al. |
| 8,200,737 | B2 | 6/2012 | Tarabzouni et al. |
| 9,322,735 | B1 | 4/2016 | Tan et al. |
| 2006/0162428 | A1 * | 7/2006 | Hu .......................... G01M 3/20 73/40.7 |
| 2008/0092061 | A1 | 4/2008 | Bankston et al. |
| 2008/0168826 | A1 | 7/2008 | Saidi et al. |
| 2011/0109464 | A1 | 5/2011 | Lepley et al. |
| 2011/0119040 | A1 | 5/2011 | McLennan |
| 2011/0161885 | A1 | 6/2011 | Gonia et al. |
| 2011/0249122 | A1 | 10/2011 | Tricoukes et al. |
| 2011/0251800 | A1 | 10/2011 | Wilkins |
| 2012/0019380 | A1 | 1/2012 | Nielsen et al. |
| 2012/0050143 | A1 | 3/2012 | Border et al. |
| 2012/0072189 | A1 | 3/2012 | Bullen et al. |
| 2012/0191349 | A1 | 7/2012 | Lenz et al. |
| 2012/0194549 | A1 | 8/2012 | Osterhout et al. |
| 2013/0179078 | A1 | 7/2013 | Griffon |

OTHER PUBLICATIONS

Turner, Bruce, "Workbook of Atmospheric Dispersion Estimates," p. 1-92. U.S. Environmental Protection Agency, Office of Air Programs. North Carolina, US. Jul. 1971.
Carlbom et al., "Planer Geometric Projections and Viewing Transformations", Computing Surveys, vol. 10:4, p. 465-502, ACM, New York, NY, Dec. 1978.
EPA, "User's Guide for the Industrial Source Complex (ISC3) Dispersion Models, vol. II—Description of Model Algorithms." p. 1-128. U.S. Environmental Protection Agency. North Carolina, US. Sep. 1995.
Rella, U.S. Appl No. 13/656,123, filed Oct. 19, 2012.
Rella, U.S. Appl No. 13/656,096, filed Oct. 19, 2012.
Rella, U.S. Appl No. 13/656,080, filed Oct. 19, 2012.
Tan, U.S. Appl. No. 13/733,864, filed Jan. 3, 2013.
Tan, U.S. Appl. No. 13/733,861, filed Jan. 3, 2013.
Tan, U.S. Appl. No. 13/733,868, filed Jan. 3, 2013.
Tan, U.S. Appl. No. 13/733,857, filed Jan. 3, 2013.
Rella, U.S. Appl. No. 13/913,359, filed Jun. 7, 2013.
Rella, U.S. Appl. No. 13/913,357, filed Jun. 7, 2013.
Keats et al., "Bayesian inference for source determination with applications to a complex urban environment," Atmospheric Environment, vol. 41, Issue 3, pp. 465-479, Jan. 2007.
Rao, Shankar K., "Source estimation methods for atmospheric dispersion," Atmospheric Environment, vol. 41, Issue 33, pp. 6964-6973, Oct. 2007.
Yee et al., "Bayesian inversion of concentration data: Source reconstruction in the adjoint representation of atmospheric diffusion," 4th International Symposium on Computational Wind Engineering, Journal of Wind Engineering and Industrial Aerodynamics, vol. 96, Issues 10-11, pp. 1805-1816, Oct. 2008.
Humphries et al., "Atmospheric Tomography: A Bayesian Inversion Technique for Determining the Rate and Location of Fugitive Emissions," Environmental Science & Technology, 46, 3, pp. 1739-1746, Dec. 12, 2011.
Steele, U.S. Appl. No. 14/139,348, filed Dec. 23, 2013.
USPTO, Office Action mailed Jun. 28, 2016 for U.S. Appl. No. 14/139,348, filed Dec. 23, 2013.
Keats, Andrew, "Bayesian inference for source determination in the atmospheric environment," University of Waterloo, Waterloo, Ontario, Canada, 2009, the year of the publication is sufficiently earlier than the effective U.S. filing date and any foreign priority date so that the particular month of publication is not in issue.
Prasad Kuldeep R., "Quantification of Methane Emissions From Street Level Data,", http://www.nist.gov/manuscript-publication-search.cfm?pub_id=914433, Abstract #A53E-0213, American Geophysical Union (AGU), Fall Meeting, San Francisco, CA, US, Dec. 9-13, 2013.
Arata C. et al., "Fugitive Methane Source Detection and Discrimination with the Picarro Mobile Methane Investigator," http://adsabs.harvard.edu/abs/2013AGUFM.A53A0150A, Abstract #A53A-0150, American Geophysical Union (AGU), Fall Meeting, San Francisco, CA, US, Dec. 9-13, 2013.
Keats, Andrew et al., "Bayesian inference for source determination with applications to a complex urban environment," http://www.sciencedirect.com/science/article/pii/S1352231006008703, Atmospheric Environment 41.3, pp. 465-479, The Netherlands, Jan. 2007.
Pavlin G. et al., "Gas Detection and Source Localization: A Bayesian Approach," http://isif.org/fusion/proceedings/Fusion_2011/data/papers/054.pdf, 14th International Conference on Information Fusion, Chicago, Illinois, US, Jul. 2011.
Crosson E. et al., "Quantification of Methane Source Locations and Emissions in an Urban Setting," http://www.slideserve.com/marly/quantification-of-methane-source-locations-and-emissions-in-an-urban-setting, uploaded on Jul. 31, 2014.
Crosson E. et al., "Quantification of Methane Source Locations and Emissions in an Urban Setting," http://adsabs.harvard.edu/abs/2011AGUFM.B51Q..04C, American Geophysical Union (AGU), Fall Meeting, San Francisco, CA, US, Dec. 5-9, 2011.
Gas Trak LTD., "Specializing in: Leak Detection Services for: Natural Gas Pipelines," http://www.slideserve.com/yama/specializing-in-leak-detection-services-for-natural-gas-pipelines, uploaded on Jul. 28, 2013.

* cited by examiner

| Surface wind speed at 10 m (m/s) | Day | | | Night | |
|---|---|---|---|---|---|
| | Incoming Solar radiation | | | Cloud Cover | |
| | Strong | Moderate | Slight | Thinly Overcast (>1/2 cloudy) | Mostly Cloudy |
| <2 | A | A-B | B | | |
| 2-3 | A-B | B | C | E | F |
| 3-5 | B | B-C | C | D | E |
| 5-6 | C | C-D | D | D | D |
| >6 | C | D | D | D | D |

FIG. 18

SYSTEMS AND METHODS FOR LIKELIHOOD-BASED MAPPING OF AREAS SURVEYED FOR GAS LEAKS USING MOBILE SURVEY EQUIPMENT

CROSS REFERENCE TO RELATED APPLICATIONS

This application claims the benefit of the filing date of U.S. Provisional Patent Application No. 61/745,562, filed on Dec. 22, 2012, titled "Systems and Methods for Likelihood-Based Detection of Gas Leaks Using Mobile Survey Equipment" which is incorporated herein by reference in its entirety.

BACKGROUND

The invention relates to systems and methods for performing field inspections of natural gas infrastructure to detect gas leaks such as methane gas leaks, and for maintaining and updating geospatial database information related to natural gas infrastructure.

A common means of distributing energy around the world is by the transmission of gas, usually natural gas. In some areas of the world manufactured gasses are also transmitted for use in homes and factories. Gas is typically transmitted through underground pipelines having branches that extend into homes and other buildings for use in providing energy for space and water heating. Many thousands of miles of gas pipeline exist in virtually every major populated area. Since gas is highly combustible, gas leakage is a serious safety concern. Recently, there have been reports of serious fires or explosions caused by leakage of gas in the United States as the pipeline infrastructure becomes older. For this reason, much effort has been made to provide instrumentation for detecting small amounts of gas so that leaks can be located to permit repairs.

One approach to gas leak detection is to mount a gas leak detection instrument on a moving vehicle, e.g., as considered in U.S. Pat. No. 5,946,095. A natural gas detector apparatus is mounted to the vehicle so that the vehicle transports the detector apparatus over an area of interest at speeds of up to 20 miles per hour. The apparatus is arranged such that natural gas intercepts a beam path and absorbs representative wavelengths of a light beam. A receiver section receives a portion of the light beam onto an electro-optical etalon for detecting the gas.

Although a moving vehicle may cover more ground than a surveyor on foot, there is still the problem of reliably and accurately locating the gas leak source (e.g., a broken pipe) if gas is detected from the vehicle.

SUMMARY

According to another aspect, a non-transitory computer-readable medium encodes instructions which, when executed by a computer system comprising at least one processor, cause the at least one processor to: identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during the first mobile measurement run would satisfy a probability condition; and update the prior 2-D surveyed area to generate a posterior 2-D surveyed area according to a second set of gas emission survey data resulting from a second mobile measurement run, the posterior 2-D surveyed area having a boundary determined such that if a potential gas emission source were located in the posterior 2-D surveyed area and had a rate of emission meeting the minimum emission rate condition, then an estimated posterior probability of detection of the potential gas emission source according to gas concentration data acquired during the first mobile measurement run and the second mobile measurement run would satisfy the probability condition.

According to another aspect, a computer system comprises at least one processor configured to: identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during the first mobile measurement run would satisfy a probability condition; and update the prior 2-D surveyed area to generate a posterior 2-D surveyed area according to a second set of gas emission survey data resulting from a second mobile measurement run, the posterior 2-D surveyed area having a boundary determined such that if a potential gas emission source were located in the posterior 2-D surveyed area and had a rate of emission meeting the minimum emission rate condition, then an estimated posterior probability of detection of the potential gas emission source according to gas concentration data acquired during the first mobile measurement run and the second mobile measurement run would satisfy the probability condition.

According to another aspect, a non-transitory computer-readable medium encodes instructions which, when executed by a computer system comprising at least one processor, cause the at least one processor to: identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during first mobile measurement run would satisfy a probability condition; and update the prior 2-D surveyed area to generate a posterior 2-D surveyed area according to a second set of gas emission survey data resulting from a second mobile measurement run, wherein updating the prior 2-D surveyed area comprises determining a posterior probability of missing detection of a potential gas source situated at a given location according to a product of: i. a prior probability of missing detection of the potential gas source situated at the given location after the first mobile measurement run, and ii. a probability of missing detection of the potential gas source situated at the given location during the second mobile measurement run.

According to another aspect, a computer system comprises at least one processor configured to: identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during first mobile measurement run would satisfy a probability condition; and update the prior 2-D surveyed area to generate a posterior 2-D surveyed area according to a second set of gas emission survey data resulting from a second mobile measurement run, wherein updating the prior 2-D surveyed area comprises determining a posterior probability of missing detection of a potential gas source situated at a given location according to a product of: i. a prior probability of missing detection of the potential gas source situated at the given location after the first mobile measurement run, and ii. a probability of missing detection of the potential gas source situated at the given location during the second mobile measurement run.

According to another aspect, a non-transitory computer-readable medium encodes instructions which, when executed by a computer system comprising at least one processor, cause the at least one processor to: receive a prior 2-D surveyed area; and update the prior 2-D surveyed area to generate a posterior 2-D surveyed area according to a set of gas emission survey data resulting from a mobile measurement run performed by a mobile measurement device along a measurement path, the set of gas emission survey data reflecting a trajectory of the first measurement path and a set of associated atmospheric condition data characterizing the mobile measurement run, wherein the posterior 2-D surveyed area is an area having a boundary such that if a potential gas emission source were located in the posterior 2-D surveyed area and had a rate of emission meeting a minimum emission rate condition, then an estimated posterior probability of detection of the potential gas emission source according to gas concentration data acquired during the mobile measurement run would satisfy a probability condition, and wherein updating the prior 2-D surveyed area comprises determining the posterior probability of missing detection of a potential gas source situated at a given location according to a product of: i. a prior probability, defined by the prior 2-D surveyed area, of missing detection of the potential gas source situated at the given location and ii. a probability of missing detection of the potential gas source situated at the given location during the mobile measurement run.

BRIEF DESCRIPTION OF THE DRAWINGS

The foregoing aspects and advantages of the present invention will become better understood upon reading the following detailed description and upon reference to the drawings where:

FIG. 18 is a table of dispersion coefficients for various atmospheric conditions according to some embodiments of the present invention.

DETAILED DESCRIPTION

Figure 1:
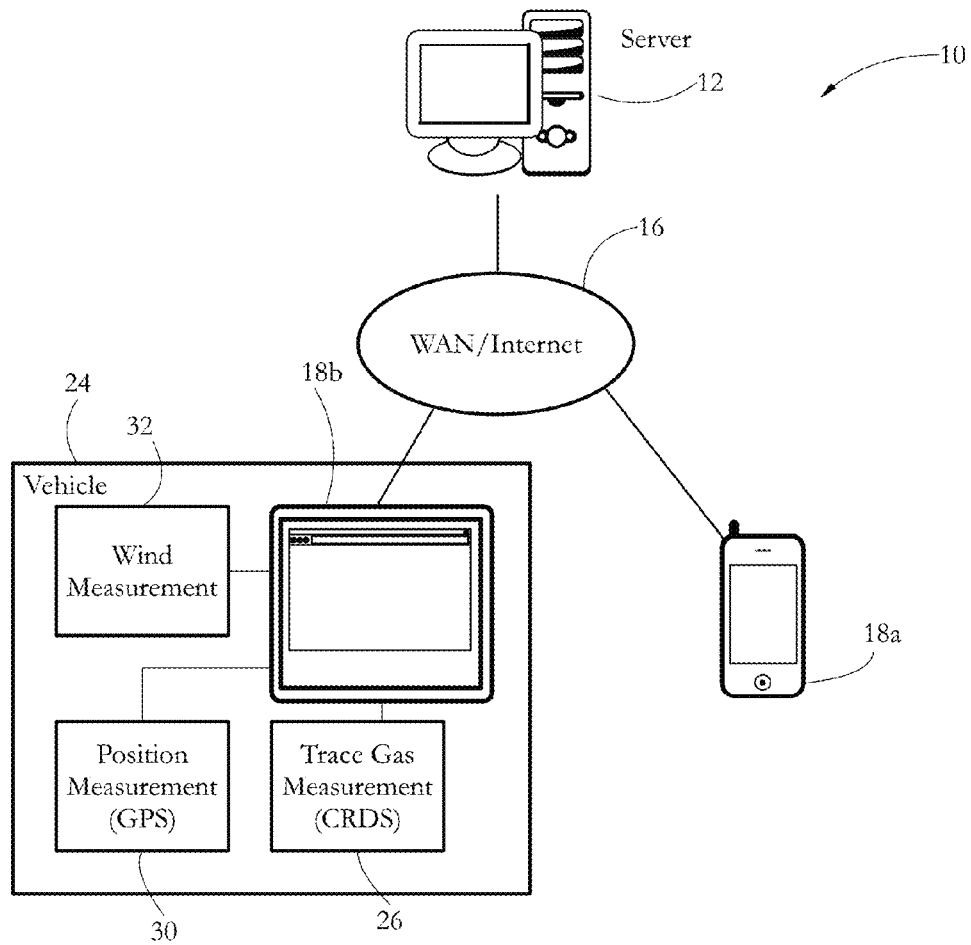
FIG. 1 shows a gas leak detection apparatus according to some embodiments of the present invention.

Apparatus and methods described herein may include or employ one or more interconnected computer systems such as servers, personal computers and/or mobile communication devices, each comprising one or more processors and associated memory, storage, input and display devices. Such computer systems may run software implementing methods described herein when executed on hardware. In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. A synthetic representation refers to an icon or other computer-generated representation, and is distinct from a real-time display of an image captured by a device camera. Unless otherwise specified, generating a 2-D map such as a heat map is understood to refer to generating a 2-D spatial distribution of values, for example a 2-D spatial distribution of probabilities that a gas emission source is present at each location along a 2-D surface, and need not include generating a display of the 2-D map. The term "natural gas" is used below to refer broadly to gases that include methane, whether or not such gasses are fossil fuels pumped out of the ground; for example, in the discussion below, sewers and landfills are described for clarity/simplicity as sources of natural gas, even though the gases generated by a landfill may not be chemically identical to gases extracted from fossil fuel geological deposits. The terms "natural gas transmission pipeline" and "natural gas distribution pipeline" are both used broadly to refer to pipelines that carry natural gas. The term "wide area network" refers to a network including at least one router. Computer programs described in some embodiments of the present invention may be stand-alone software entities or sub-entities (e.g., subroutines, code objects) of other computer programs. Computer readable media encompass storage (non-transitory) media such as magnetic, optic, and semiconductor media (e.g. hard drives, optical disks, flash memory, DRAM), as well as communications links such as conductive cables and fiber optic links. According to some embodiments, the present invention provides, inter alia, computer systems programmed to perform the methods described herein, as well as computer-readable media encoding instructions to perform the methods described herein.

Finding and grading leaks in a natural gas distribution system using traditional means is slow and costly. There is increasing interest on the part of gas utilities and public utility commissions to improve means to find natural gas leaks quickly and with high detection efficiency. Furthermore, according to a Federal law passed in 2009, utilities in the United States must put in place processes to quantitatively assess risks to their distribution systems. The results of such assessments may then be used, presumably, to prioritize resources and inform other decisions to ensure public safety.

According to one aspect, when an elevated concentration of methane that is consistent with the signature of a gas plume is detected by a measurement system as described below, software reports the amplitude of the background-subtracted maximum concentration and a range of directions toward the likely source of gas emission. Additionally, the software displays a Field of View swath indicating which areas of the survey region have been covered and which have not. A surveyed area output is suitable for incorporation into a risk model, and has to potential to remove much of the human bias that is currently introduced into such models associated with how leak surveys are currently conducted and how survey coverage is accounted for. Reducing such bias allows improving the accuracy of risk calculations and allows for better-informed decision-making Systems and methods described below allow generating and/or updating 2-D spatial distributions (heat maps) of probabilities that facilitate the detection of natural gas leaks. For example, such spatial distributions may be heat maps of probabilities that a source is present at a given location, and/or probabilities that a source would have been detected had it been present at a given location, during one or more measurement runs.

Exemplary Hardware and Software Environment

FIG. 1 shows a gas detection and display system 10 according to some embodiments of the present invention. System 10 comprises a service provider server computer system 12 and a set of client computer systems 18a-b, all connected through a wide area network 16 such as the Internet. Server computer system 12 may include multiple physical servers of one or more service providers; for example, one service provider may provide map and street view data, while another service provider may provide infrastructure (e.g. plats), and real-time and/or historical gas concentration and wind direction and speed data. Client computer systems 18a-b may be portable computing devices such as laptops, smartphones, tablet computers and the like. A vehicle 24 such as an automobile may be used to carry at least some client computer systems (e.g. an exemplary client computer system 18b) and associated hardware including a gas analyzer 26, a location/GPS measurement device 30, and a wind measurement device 32. Gas analyzer 26 may be a Picarro analyzer using Wavelength-Scanned Cavity Ring Down Spectroscopy (CRDS), available from Picarro, Inc., Santa Clara, Calif. Such analyzers may be capable of detecting trace amounts of gases such as methane, acetylene, carbon monoxide, carbon dioxide, hydrogen sulfide, and/or water. In particular applications suited for detection of natural gas leaks, a Picarro G2203 analyzer capable of detecting methane concentration variations of 3 ppb may be used. Wind measurement device 32 may include a wind anemometer and a wind direction detector (e.g. wind vane). GPS measurement device 30 may be a stand-alone device or a device built into client computer system 18b.

Figure 2:
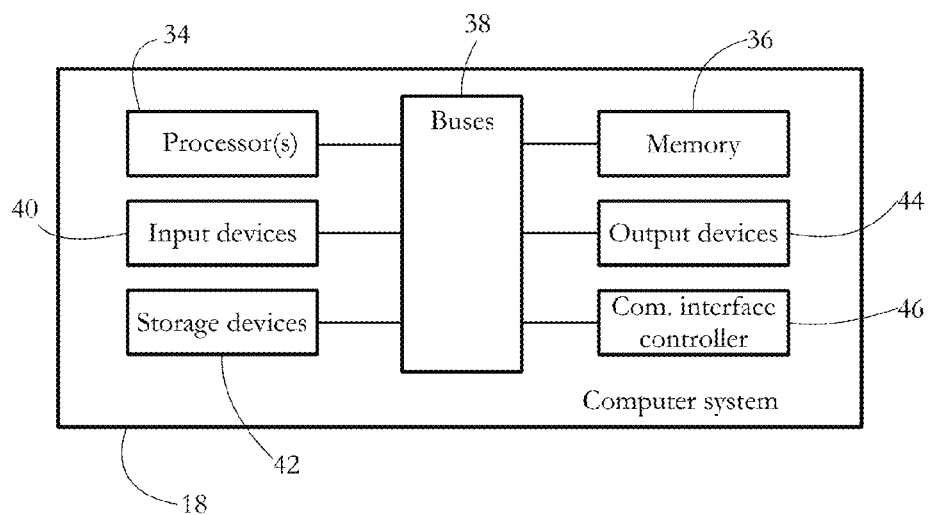
FIG. 2 illustrates hardware components of a computer system according to some embodiments of the present invention.

Each computer system 18 comprises a plurality of hardware components, schematically illustrated in FIG. 2. Such computer systems may be devices capable of web browsing and thus access to remotely-hosted protected websites, such as desktop, laptop, tablet computer devices, or mobile phones such as smartphones. In some embodiments, computer system 18 comprises one or more processors 34, a memory unit 36, a set of input devices 40, a set of output devices 44, a set of storage devices 42, and a communication interface controller 46, all connected by a set of buses 38. In some embodiments, processor 34 comprises a physical device (e.g. multi-core integrated circuit) configured to execute computational and/or logical operations with a set of signals and/or data. In some embodiments, such logical operations are delivered to processor 34 in the form of a sequence of processor instructions (e.g. machine code or other type of software). Memory unit 36 may comprise random-access memory (RAM) storing instructions and operands accessed and/or generated by processor 34. Input devices 40 may include touch-sensitive interfaces, computer keyboards and mice, among others, allowing a user to introduce data and/or instructions into system 18. Output devices 44 may include display devices such as monitors. In some embodiments, input devices 40 and output devices 44 may share a common piece of hardware, as in the case of touch-screen devices. Storage devices 42 include computer-readable media enabling the storage, reading, and writing of software instructions and/or data. Exemplary storage devices 42 include magnetic and optical disks and flash memory devices, as well as removable media such as CD and/or DVD disks and drives. Communication interface controller 46 enables system 18 to connect to a computer network and/or to other machines/computer systems. Typical communication interface controllers 46 include network adapters. Buses 38 collectively represent the plurality of system, peripheral, and chipset buses, and/or all other circuitry enabling the inter-communication of devices 34-46 of computer system 18.

Figure 3:
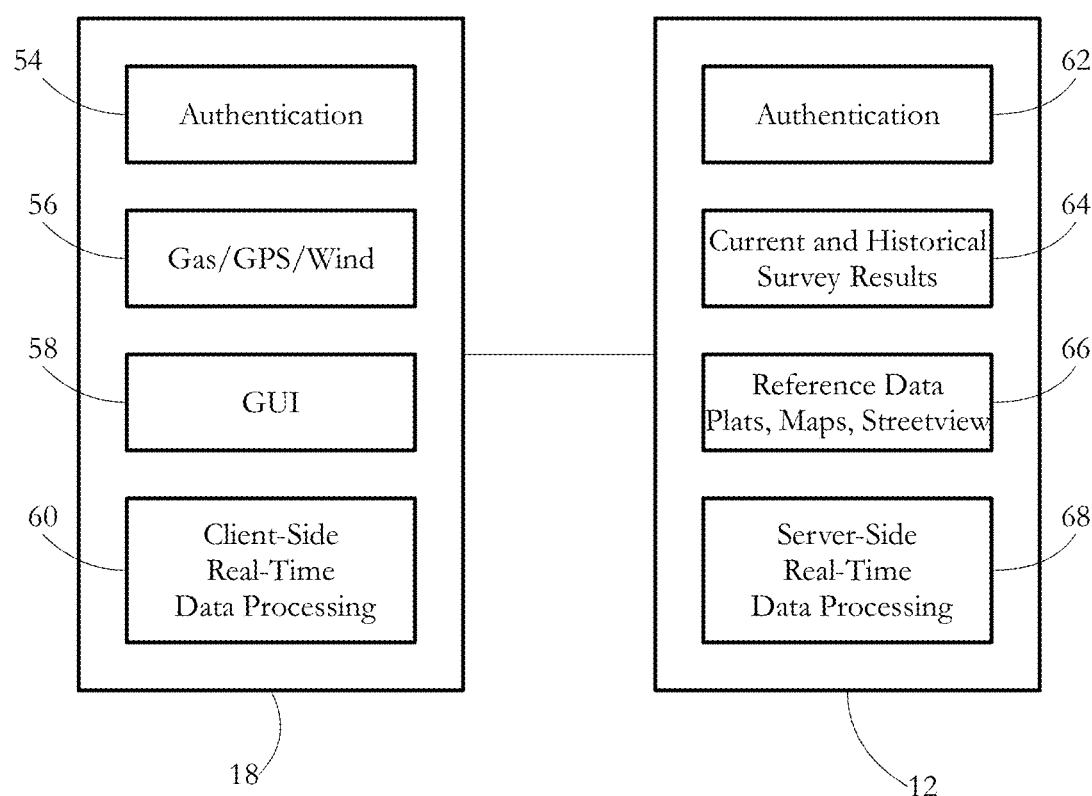
FIG. 3 shows a number of application or modules running on a client computer system and a corresponding server computer system according to some embodiments of the present invention.

FIG. 3 shows a number of applications or modules running on an exemplary client computer system 18 and corresponding server computer system 12. Authentication applications 54, 62 are used to establish secure communications between computer systems 12, 18, allowing client computer system 18 selective access to the data of a particular customer or user account. A client data collection module 56 collects real-time gas concentration, location data such as global positioning system (GPS) data, as well as wind speed and wind direction data. A client GUI module 58 is used to receive user input and display results as described herein. A client-side real-time data processing module 60 is used to perform at least some of the data processing described herein to generate survey results from input data. Other data processing may be performed by a server-side data processing module 68. Server computer system 12 also maintains one or more application modules and/or associated data structures storing current and past survey results 64, as well as application modules and/or data structures storing reference data 66 such as plats indicating the geographic locations of natural gas pipelines, map data, and street view images.

Exemplary GUI Design

Figure 4:
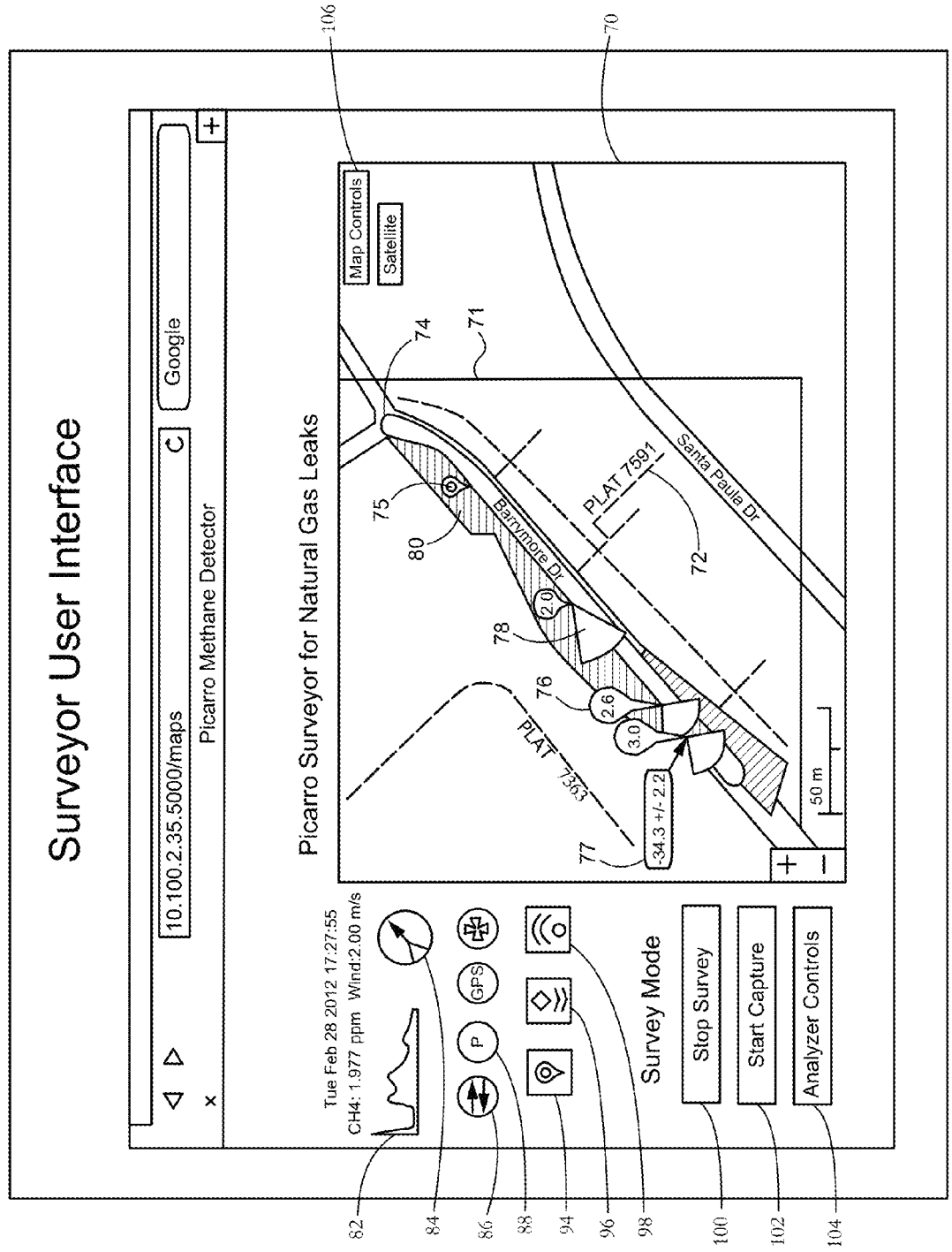
FIG. 4 is a schematic drawing of a screen shot on a graphical user interface displaying survey results on a street map according to some embodiments of the present invention.

FIG. 4 is a schematic drawing of a screen shot on a graphical user interface, displaying survey results on a street map 70 according to some embodiments of the present invention. The GUI screenshots may be displayed on a client device in the vehicle, which may be connected to a server as described above. The illustrated screenshots show both exemplary user input, which may be used to control system operation, and exemplary real-time displays of collected/processed data. In the example, the display includes the geo-referenced street map 70 showing plat lines 72. The plat lines 72 are preferably derived from gas company records. An active pipeline plat boundary 71 may also be displayed on the map 70. A user-selectable button 96 may be selected to overlay a selected pipeline plat on the map 70. Superimposed on the map 70 are one or more lines (preferably in a distinguishing color not shown in patent drawings) indicating the path 74 driven by the vehicle with the mobile gas measurement device on one or more gas survey routes. In this example, the path 74 shows the vehicle U-turned at the Y-shaped intersection. Optionally, a current location icon 75 may be overlaid on the map 70 to indicate the current surveyor location, e.g., the position of the vehicle with a gas measurement device and wind measurement device. A user-selectable button 94 may be selected to center the map 70 by current surveyor location. Also provided is a user-selectable start button 102 and stop button 100 to start/stop capturing gas for analysis. An analyzer control button 104 is user-selectable to control analyzer operations (e.g., shut down, start new trace, run isotopic analysis, etc.).

Peak markers 76 show the locations along the path 74 where peaks in the gas concentration measurements, which satisfy the conditions for being likely gas emission indications, were identified. The colors of the peak markers 76 may be used to distinguish data collected on different runs. The annotations within the peak markers 76 show the peak concentration of methane at the locations of those measurement points (e.g., 3.0, 2.6, and 2.0 parts per million). An isotopic ratio marker 77 may be overlaid on the map 70 to indicate isotopic ratio analysis output and tolerance (e.g., −34.3+/−2.2). Also displayed on the map 70 are search area indicators 78, preferably shown as a sector of a circle having a distinguishing color. Each of the search area indicators 78 indicates a search area suspected to have a gas emission (e.g. leak) source. The opening angle of the search area indicator 78 depicts the variability in the wind direction. The orientation of the axis of the search area indicator 78 (preferably an axis of symmetry) indicates the likely direction to the potential gas leak source. Also displayed on the map 70 are one or more surveyed area indicators 80 (shown as hatched regions in FIG. 4) that indicate a survey area for a potential gas leak source. The surveyed area indicator 80 adjoins path 74 and extends in a substantially upwind direction from the path 74. The survey area marked by each indicator 80 is preferably displayed as a colored swath overlaid or superimposed on the map 70. For example, the colored swaths may be displayed in orange and green for two runs. In preferred embodiments, the parameters of the search area indicators 78 and the survey area indicators 80 (described in greater detail below) are generated according to measurements of wind direction and speed, the velocity of the vehicle, and optionally the prevailing atmospheric stability conditions.

Referring still to FIG. 4, the surveyor user interface may also include a real-time CH4 concentration reading 82. A wind indicator symbol 84 may display real-time wind information, which may be corrected for the velocity vector of the vehicle to represent the true wind rather than the apparent wind when the vehicle is in motion. Average wind direction is indicated by the direction of the arrow of the wind indicator symbol 84, while wind direction variability is indicated by the degree of open angle of the wedge extending from the bottom of the arrow. Wind speed is indicated by the length of the arrow in the wind indicator symbol 84. An internet connection indicator 98 blinks when the internet connection is good. A data transfer status button 86 is user-selectable to display data transfer status (e.g., data transfer successful, intermittent data transfer, or data transfer failed). An analyzer status button 88 is user-selectable to display current analyzer status such as cavity pressure, cavity temperature, and warm box temperature. A map control button 106 is user-selectable to open a map controls window with user-selectable layer options, discussed below with reference to FIG. 7.

Figure 5:
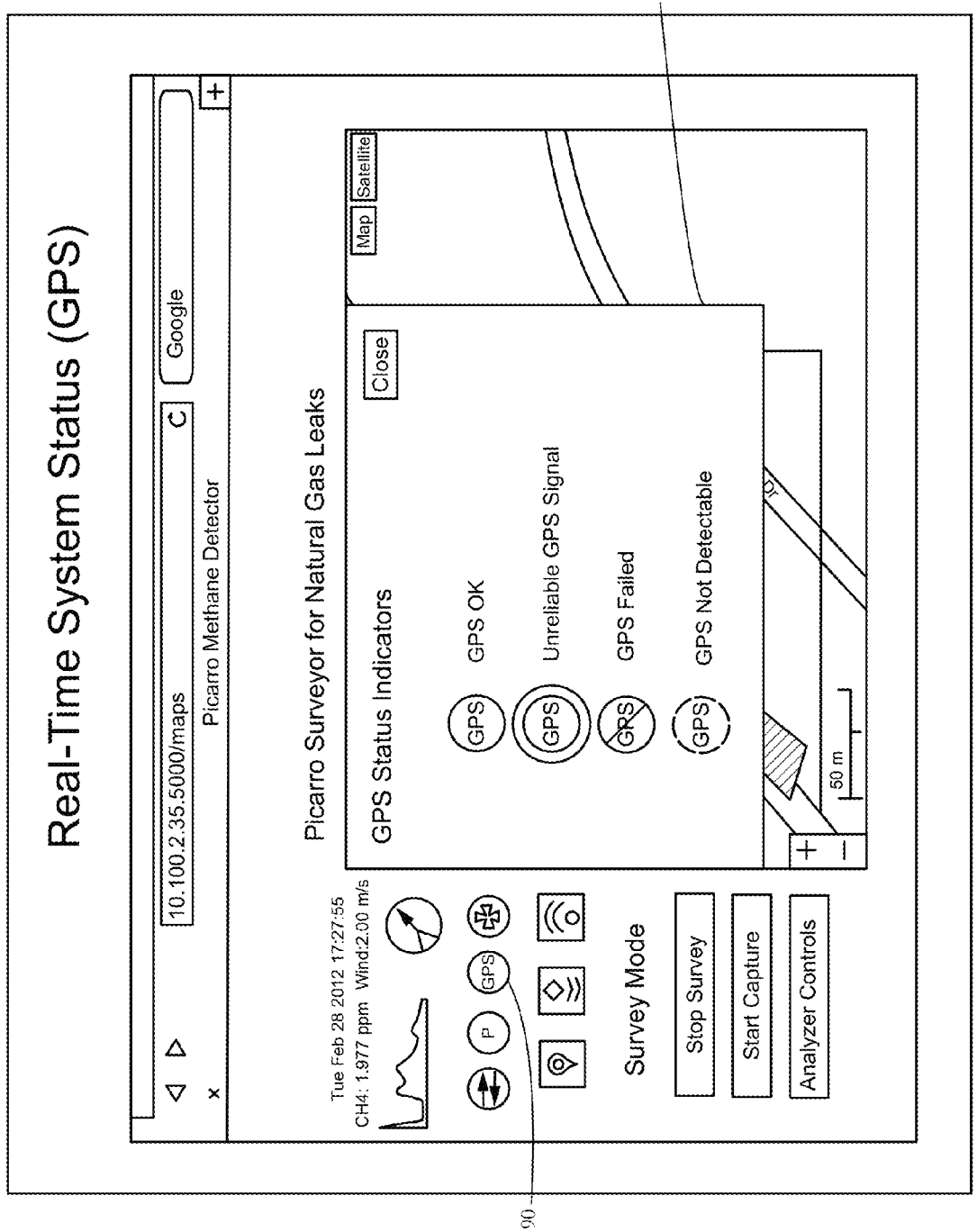
FIG. 5 is a schematic drawing of a screen shot on a graphical user interface with GPS indicators according to some embodiments of the present invention.

FIG. 5 is a schematic drawing of a screen shot on the graphical user interface, displaying a GPS status window 91, according to some embodiments of the present invention. A user-selectable GPS status button 90 may be selected to open the GPS status window 91. The GPS status window 91 preferably includes indicators of the current GPS status, such as "GPS OK", "Unreliable GPS signal", "GPS Failed", or "GPS Not Detectable".

Figure 6:
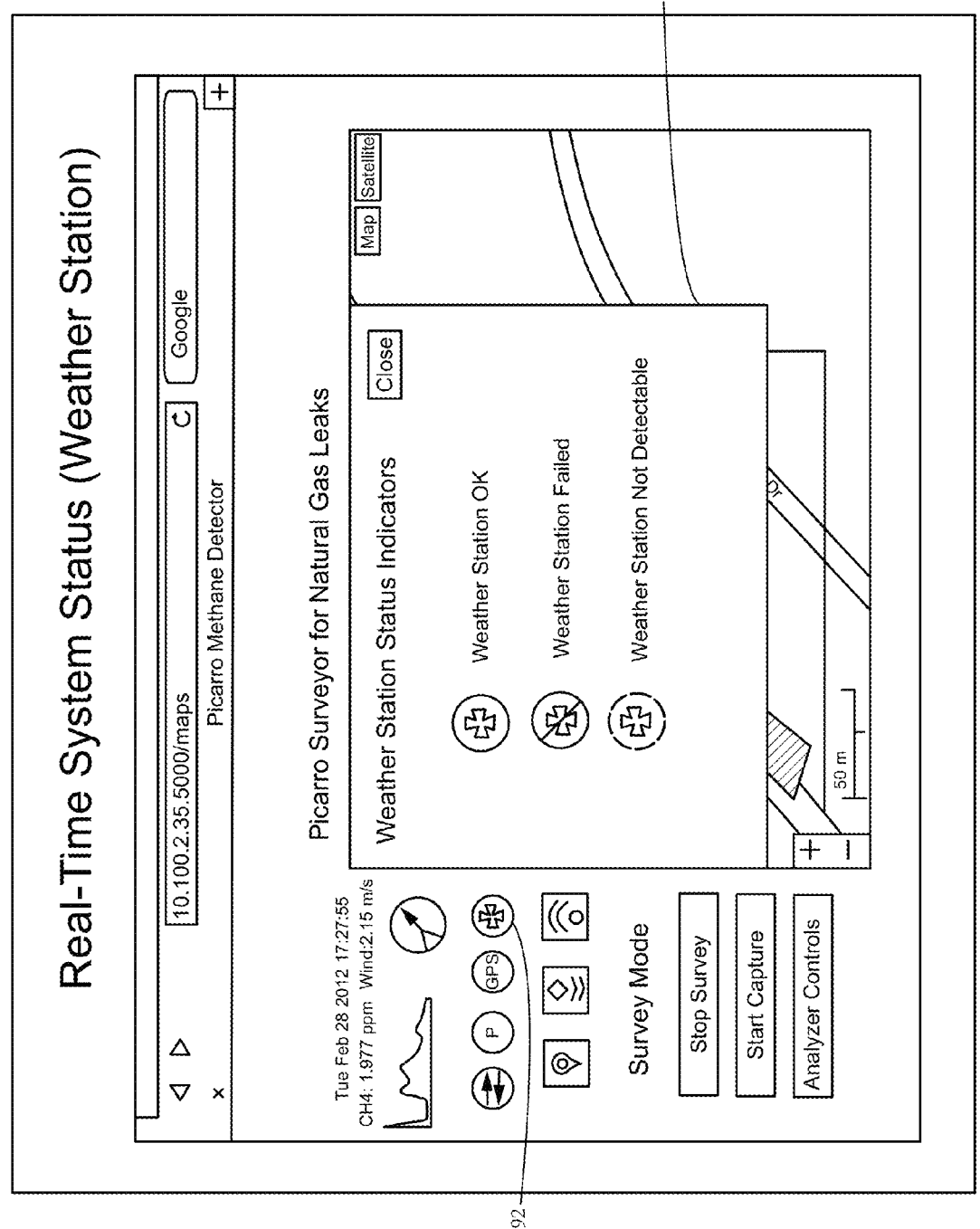
FIG. 6 is a schematic drawing of a screen shot on a graphical user interface with weather station status indicators according to some embodiments of the present invention.

FIG. 6 is a schematic drawing of a screen shot on the graphical user interface, displaying a weather station status window 93, according to some embodiments of the present invention. A user-selectable weather station status button 92 may be selected to open the weather station status window 93. The weather station status window 93 preferably includes indicators of the current weather station status, such as "Weather Station OK", "Weather Station Failed", or "Weather Station Not Detectable". Weather station data are preferably received in real-time and may include wind data and atmospheric stability conditions data relevant to the area being surveyed.

Figure 7:
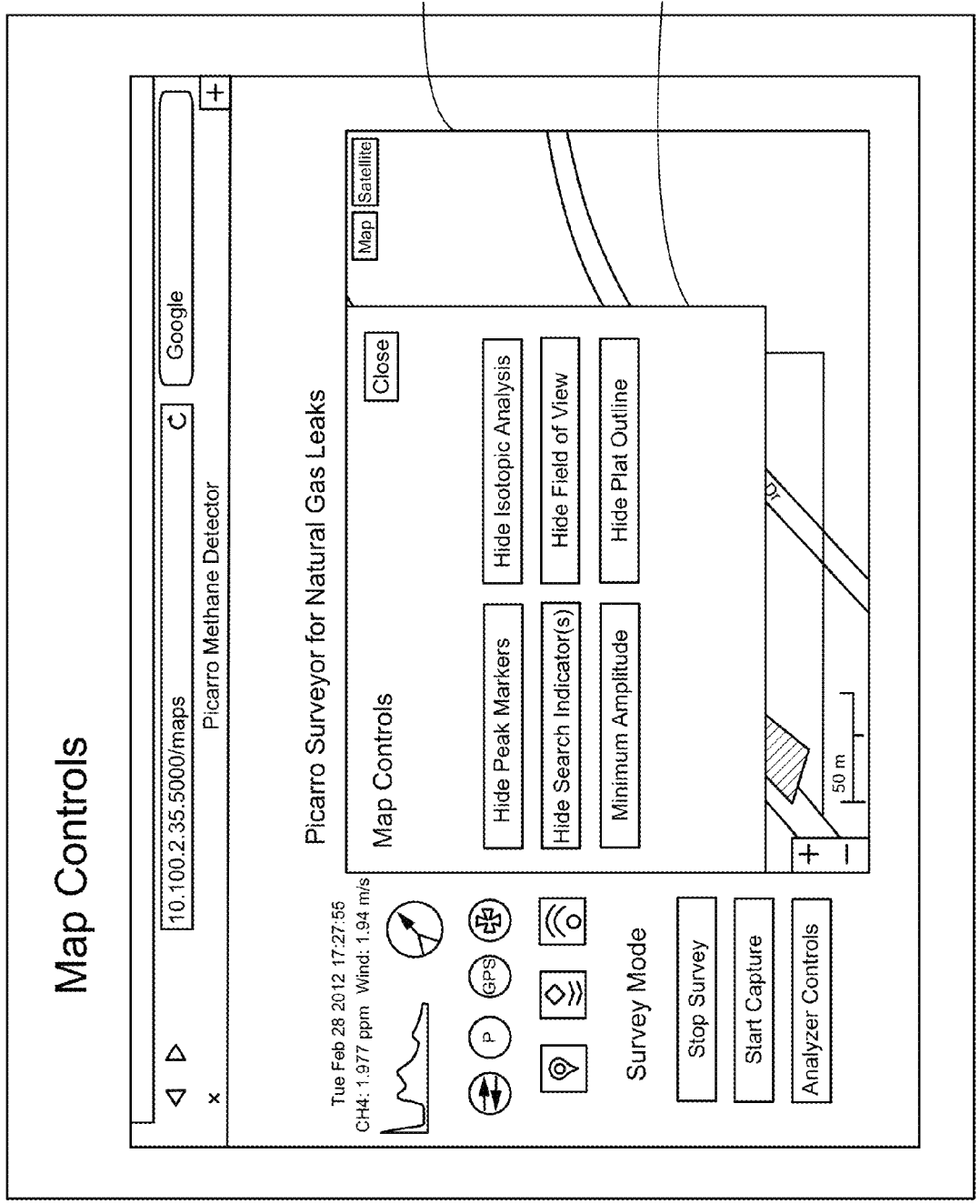
FIG. 7 is a schematic drawing of a screen shot on a graphical user interface with map controls according to some embodiments of the present invention.

FIG. 7 is a schematic drawing of a screen shot on the graphical user interface, displaying a map control window 95. Various elements displayed on the map 70 are regarded as layers which may be turned on or off. In this example, map controls window 95 includes six user-selectable buttons named "Hide Peak Markers", "Hide Search Area Indicators", "Minimum Amplitude", "Hide Isotopic Analysis", "Hide Field of View", and "Hide Plat Outline". The "Hide Peak Markers" button may be selected so that the markers indicating peak gas concentration measurements are not displayed on the map 70. The "Hide Search Area Indicators" button may be selected so that the search area indicators are not displayed on the map 70. The "Minimum Amplitude" button may be selected so that gas concentration peaks not meeting a minimum amplitude requirement are not displayed on the map 70. The "Hide Isotopic Analysis" button may be selected so that isotopic ratio analysis information is not displayed on the map 70 next to the peak markers. The "Hide Field of View" button may be selected so that the survey area indicator(s) are not displayed on the map 70. The "Hide Plat Outline" button may be selected so that the plat lines are not displayed on the map 70.

Exemplary Gas Emission Data Collection and Analysis

Figure 8:
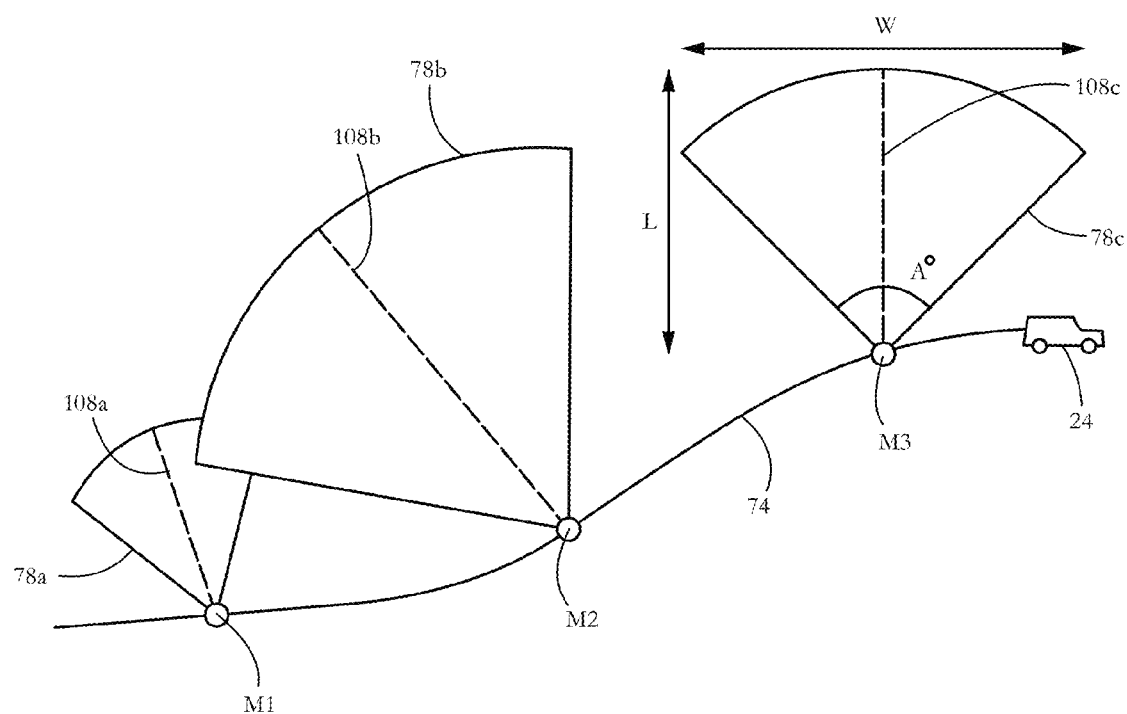
FIG. 8 is a schematic diagram of three search area indicators according to some embodiments of the present invention.

FIG. 8 is a schematic diagram of three search area indicators 78a, 78b, and 78c according to some embodiments of the present invention. Each of the search area indicators 78a, 78b, and 78c has a respective axis 108a, 108b, and 108c indicating a representative wind direction relative to a geo-referenced location of a corresponding gas concentration measurement point M1, M2, and M3. The gas concentration measurement points M1, M2, and M3 are positioned along the path 74 traveled by the vehicle 24 that carries a GPS device, a mobile gas measurement device, and wind measurement device for taking wind direction measurements and wind speed measurements. Each of the search area indicators, such as the search area indicator 78c, preferably has a width W relative to its axis 108c. The width W is indicative of a wind direction variability associated with wind direction measurements in the area of the gas concentration measurement point M3. In preferred embodiments, the width W is indicative of a variance or standard deviation of the wind direction measurements. Also in preferred embodiments, the search area indicator 78c has the shape of a sector of a circle, with the center of the circle positioned on the map at the location of the gas concentration measurement point M3. Most preferably, the angle A subtended by the sector of the circle is proportional to a standard deviation of the wind direction measurements taken at or nearby the measurement point M3. For example, the angle A may be set to a value that is twice the angular standard deviation of the wind direction measurements. It is not necessary to display the gas concentration measurement points M1, M2, and M3 on the map along with the search area indicators 78a, 78b, and 78c. As previously shown in FIGS. 4 and 7, the measurement points and associated gas concentration measurements are preferably map layer options for an end-user that may be turned on or off.

Referring again to FIG. 8, the axis 108c of the search area indicator 78c is preferably an axis of symmetry and points in a representative wind direction relative to the gas concentration measurement point M3. The representative wind direction may be a mean, median or mode of the wind direction measurements taken at or nearby the measurement point M3, and indicates the likely direction to a potential gas leak source. The wind direction measurements may be taken from the vehicle 24 as it moves and converted to wind direction values relative to the ground (e.g., by subtracting or correcting for the velocity vector of the vehicle). In some embodiments, the axis 108c has a length L indicative of a maximum detection distance value representative of an estimated maximum distance from a potential gas leak source at which a gas leak from the source can be detected. For example, the length may be proportional to the maximum detection distance value, or proportional to a monotonically increasing function of the maximum detection distance value, such that longer maximum detection distance values are represented by longer axis lengths. In preferred embodiments, the maximum detection distance value and corresponding length L are determined according to data representative of wind speed in the search area. In some embodiments, the maximum detection distance value and the corresponding length L are determined according to data representative of atmospheric stability conditions in the search area. Each of the search area indicators 78a, 78b, and 78c may thus provide a visual indication of a likely direction and estimated distance to a potential gas leak source.

Although a sector of a circle is the presently preferred shape for a search area indicator, alternative shapes for a search area indicator include, but are not limited to, a triangle, a trapezoid, or a wedge.

Figure 9:
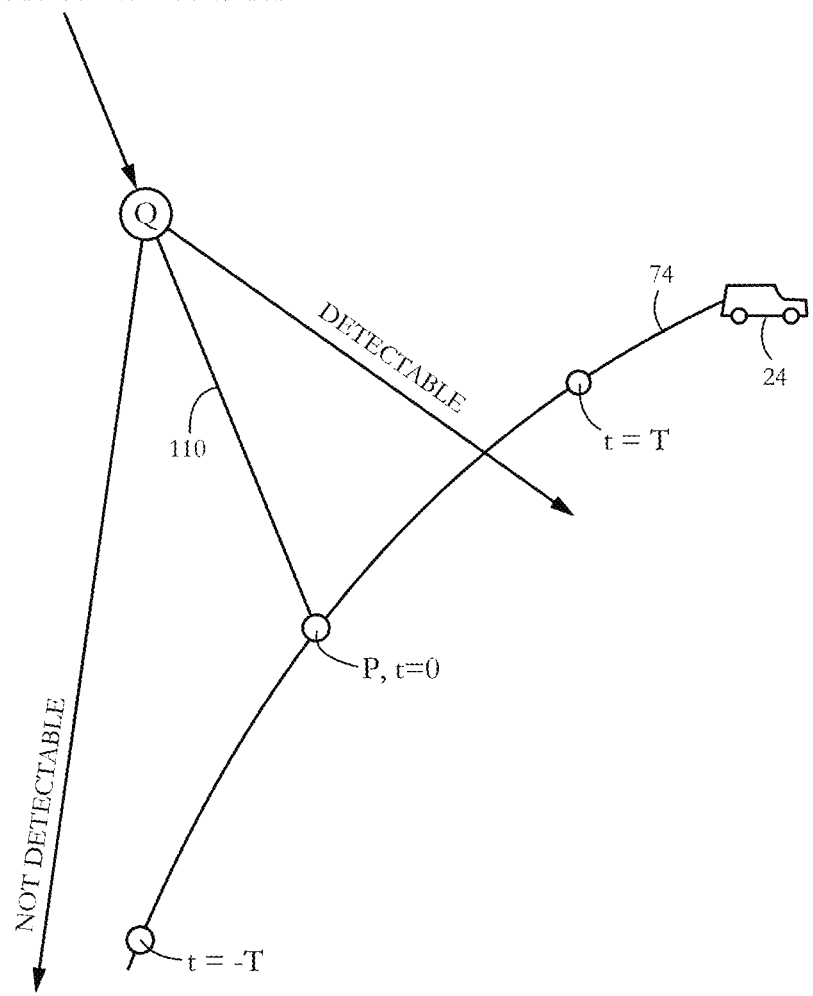
FIG. 9 is a schematic diagram illustrating wind lines relative to the path of a mobile gas measurement device for detecting or not detecting a gas leak from a potential gas leak source according to some embodiments of the present invention.

FIG. 9 is a schematic diagram illustrating an example of detecting or not detecting a gas leak from a potential gas leak source, according to some embodiments of the present invention. An indicator of a surveyed area (also sometimes referred to as a "field of view" below) provides an indication of how well the measurement process has surveyed the area around the path 74 traveled by the vehicle 24 that carries a GPS device, a mobile gas measurement device, and wind measurement device. The surveyed area indicator is designed such that if a potential gas emission (e.g. leak) source is located in the survey area and has a rate of emission meeting a minimum emission rate condition, then an estimated probability of detection of a gas emission from the potential gas emission source at one or more measurement points P along the path 74 satisfies a probability condition.

Whether or not a potential gas emission source of a given strength is detectable by a gas measurement device of a given sensitivity depends on the separation distance of the source from the gas measurement device and on whether the wind is sufficient to transport gas from the gas emission source to the gas measurement device at some point along the path 74. In some embodiments, a physical model is employed that relates the measured gas concentration peak at the location of the vehicle 24 (in ppm, for example) to the emission rate of the potential gas emission source (in g/sec, for example) and the distance between the source and the detection point.

There are multiple possible models that describe the propagation of a gas emission as a plume through the atmosphere. One well-validated physical model for a plume (Gifford, F. A., 1959. "Statistical properties of a fluctuating plume dispersion model". Adv. Geophys, 6, 117-137) is to model the plume as a Gaussian distribution in the spatial dimensions transverse to the wind direction. For a ground level source, the concentration c (x, y, z) at a distance x downwind, y crosswind, and at a height z from a gas emission source of strength Q located on the ground is then given by Equation (1):

$$C(x, y, z) = \frac{Q}{\pi v \sigma_y \sigma_z} e^{-y^2/2\sigma_y^2 - z^2/2\sigma_z^2} \quad [1]$$

where v is the speed of the wind, and the plume dispersion half-widths $\sigma_y$ and $\sigma_z$ depend on x via functions that are empirically determined for various atmospheric stability conditions.

If we consider the plume center, where y=z=0, the concentration at the center is given by Equation (2):

$$C_{peak} = \frac{Q}{\pi v \sigma_y \sigma_z} \quad [2]$$

The dimensions of the Gaussian distribution horizontally and vertically, half-widths $\sigma_y$ and $\sigma_z$, increase with increasing distance from the source. The amount they increase can be estimated from measurements of wind speed, solar irradiation, ground albedo, humidity, and terrain and obstacles, all of which influence the turbulent mixing of the atmosphere. However, if one is willing to tolerate somewhat more uncertainty in the distance estimation, the turbulent mixing of the atmosphere can be estimated simply from the wind speed, the time of day, and the degree of cloudiness, all of which are parameters that are available either on the vehicle 24 or from public weather databases in real time. Using these available data, estimates of the Gaussian width parameters can be estimated using the Pasquill-Gifford-Turner turbulence typing scheme (Turner, D. B. (1970). "Workbook of atmospheric dispersion estimates". US Department of Health, Education, and Welfare, National Center for Air Pollution Control), or modified versions of this scheme.

For a given sensitivity of the gas measurement device, there is a minimum concentration which may be detected. Given a gas emission source of strength greater than or equal to the minimum concentration, the source will be detected if it is closer than an estimated maximum distance $X_{max}$, where this is the distance such that $\sigma_y \sigma_z = Q/(\pi v c)$. If the wind is blowing gas directly from the gas emission source to the gas measurement device, the estimated maximum distance $X_{max}$ is the distance beyond which the source may be missed. This estimated maximum detection distance may depend upon atmospheric stability conditions as well as wind speed. The formula diverges to infinity when the wind speed is very small, so in some embodiments it may be advisable to set a lower limit (e.g., 0.5 m/s) for this quantity.

The minimum emission rate $Q_{min}$ is determined by the requirements of the application. For natural gas distribution systems, a minimum leak rate of 0.5 scfh (standard cubic feet per hour) may be used; below this level, the leak may be considered unimportant. Other minimum leak rates (e.g. 0.1 scfh, 1 scfh, or other values within or outside this range) may be used for natural gas or other leak detection applications. The minimum detection limit of the plume $C_{min}$ is given either by the gas detection instrument technology itself, or by the spatial variability of methane in the atmosphere when emissions are not present. A typical value for $C_{min}$ is 30 ppb (parts-per-billion) above the background level (typically 1,800 ppb). Given these two values for $Q_{min}$ and $C_{min}$, and by predicting $\sigma_y$ and $\sigma_z$ given atmospheric measurements (or with specific assumptions about the state of the atmosphere, such as the stability class), one may then determine the estimated maximum detection distance $X_{max}$ by determining the value for $X_{max}$ that satisfies the following equality, Equation (3):

$$C_{min} = \frac{Q_{min}}{\pi v \sigma_y \sigma_z}. \quad [3]$$

In some embodiments the relationship between $\sigma_y$ and $\sigma_z$ and $X_{max}$ is provided by a functional relationship, a lookup table, or similar method. Because $\sigma_y$ and $\sigma_z$ are monotonically increasing functions of $X_{max}$, a unique value can be determined from this process. For example, one useful functional form is a simple power law, where the coefficients a, b, c, and d depend on atmospheric conditions: $\sigma_y = ax^b$; $\sigma_z = cx^d$.

In some embodiments, the concentration C measured close to the ground of a Gaussian plume due to a gas leak source on the ground depends on the rate of emission Q of the source, the distance x between the source and the gas measurement device, and the speed of the wind blowing from the source to the gas measurement device, in accordance with an expression of the form (Equation 4):

$$C = \frac{Q}{\pi v \sigma_y(x) \sigma_z(x)} \qquad [4]$$

The expressions for $\sigma_y(x)$ and $\sigma_z(x)$ depend on the stability class of the atmosphere at the time of measurement. In some embodiments, the stability class of the atmosphere is inferred from the answers to a set of questions given to the operator, or from instruments of the vehicle, or from data received from public weather databases. As shown in the table of FIG. 18, coefficients A, B, C, D, E and F may depend on surface wind speed and atmospheric conditions such as day or night, incoming solar radiation, and cloud cover. Mathematical forms for $\sigma_y(x)$ and $\sigma_z(x)$ are documented in Section 1.1.5 of the User's Guide for Industrial Source Complex (ISC3), Dispersion Models Vol. 2 (US Environmental Protection Agency document EPA-454/B955-003b September 1995). Given the sensitivity of the gas measurement device and the rate of emission of the smallest potential gas leak source of interest, equation (4) may be solved to find the estimated maximum distance $X_{max}$ beyond which a potential gas leak source may be missed by the gas measurement device.

Figure 16:
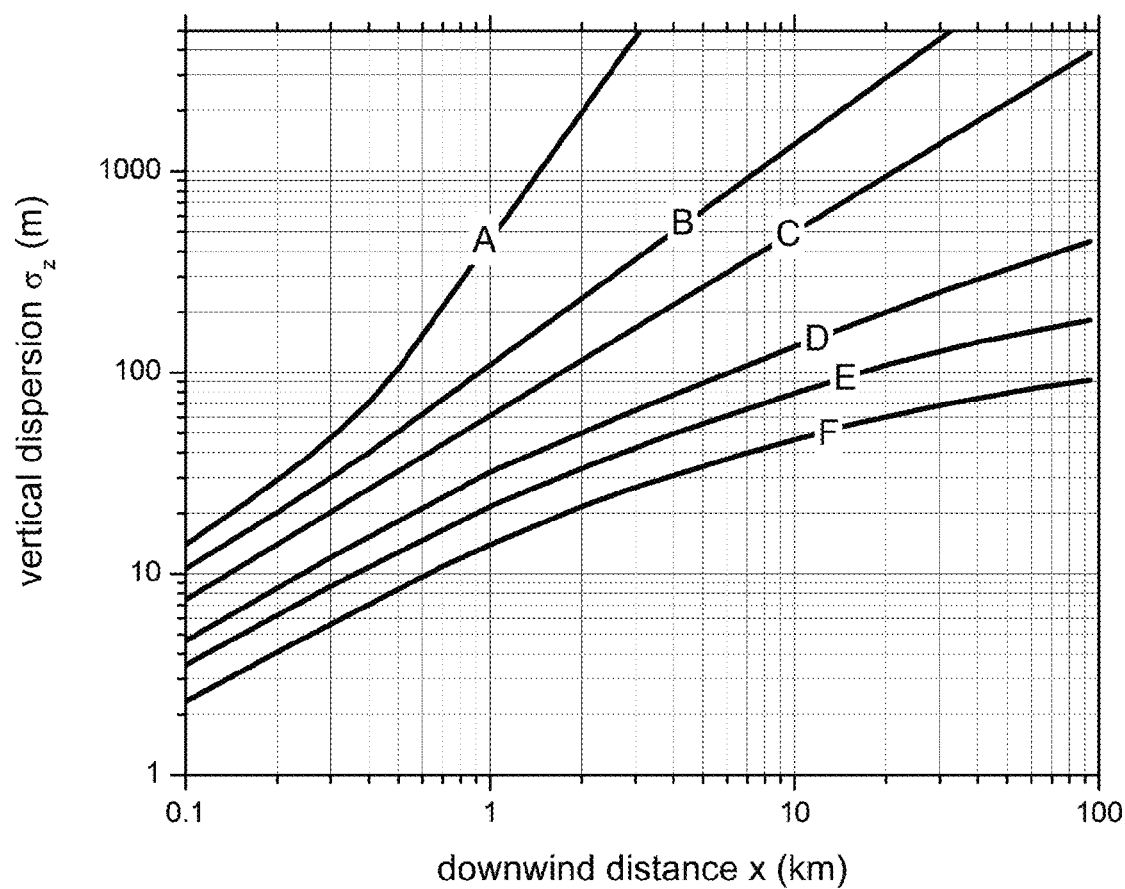
FIG. 16 is a graph of vertical dispersion coefficients of a gas plume as a function of downwind distance from a gas leak source according to some embodiments of the present invention.
Figure 17:
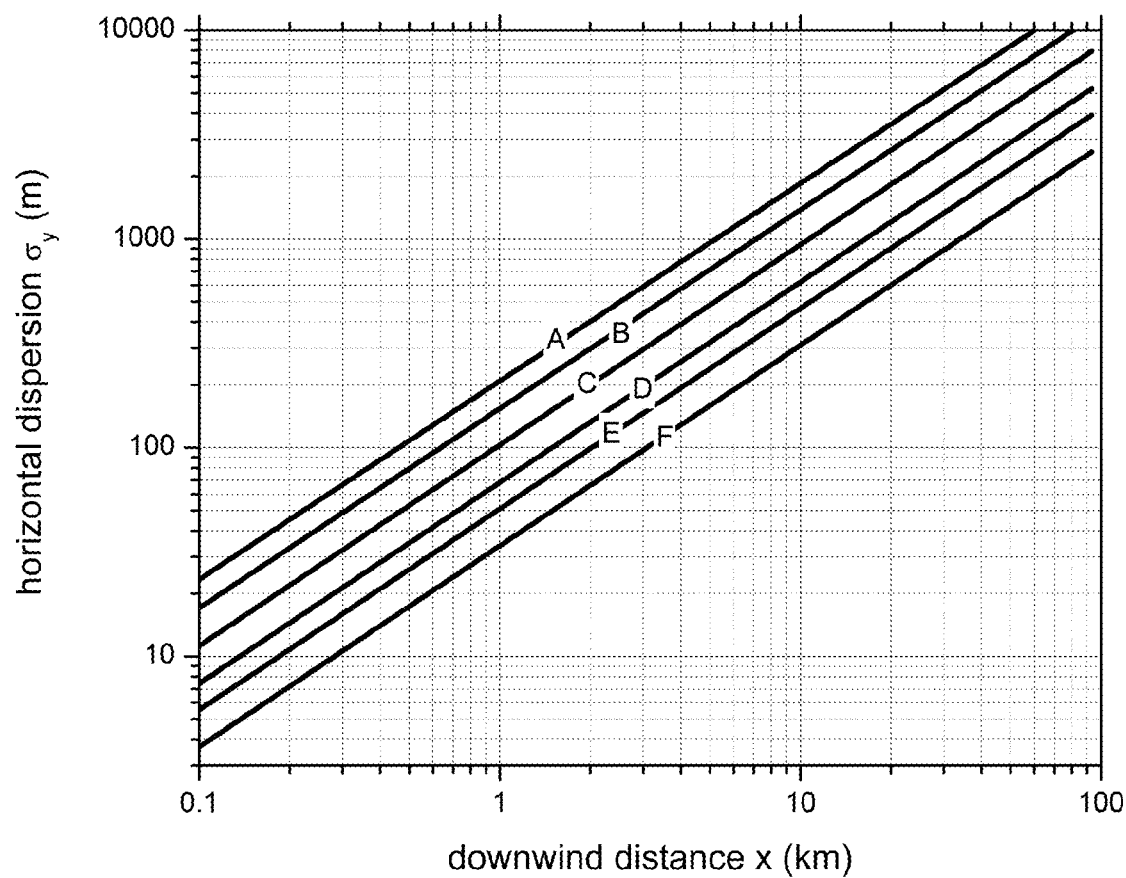
FIG. 17 is a graph of crosswind dispersion coefficients of a gas plume as a function of downwind distance from a gas leak source according to some embodiments of the present invention.

FIG. 16 is a graph of vertical $\sigma_z(x)$ dispersion coefficients of a gas plume as a function of downwind distance from a gas leak source according to some embodiments of the present invention. FIG. 17 is a graph of crosswind $\sigma_y(x)$ dispersion coefficients of a gas plume as a function of downwind distance from a gas leak source according to some embodiments of the present invention. The graphs are from from de Nevers, 2000, Air Pollution Control Engineering, The McGraw-Hill Companies, Inc. The dispersion coefficients are functions of downwind distance x. In this example, dispersion coefficients are calculated based on atmospheric stability. The table of FIG. 18 gives the atmospheric stability class as a function of wind speed, day or night, cloud cover, and solar radiation. In some embodiments, the dispersion coefficients and/or the estimated maximum distance $X_{max}$ may depend upon an urban or rural environment for the gas concentration measurements and plume dispersion. For example, the estimated maximum distance $X_{max}$ may be less in an urban environment with buildings or other structures than in a rural environment.

The actual distance at which a gas emission source may be detected is reduced if there is some variability or uncertainty in the direction of the wind. This is because there is a probability that the wind blows gas in a direction such that it does not intercept the path 74 of the vehicle 24 (FIG. 9). In practice this uncertainty is usually larger than the intrinsic angular uncertainty $\sigma_y/x$ implied by the Gaussian plume model. In order to determine the effective survey area of the mobile gas measurement device, assume for this example that the wind speed remains approximately constant within a time interval $-T<t<T$ bounding the time $t=0$ at which the vehicle 24 passes through a particular point P on the path 74, but that the wind direction (angle) is distributed as a Gaussian with a known mean and standard deviation.

As shown in FIG. 9, we consider the line 110 through the measurement point P pointing toward the direction of the mean wind, and whether a candidate point Q on this line qualifies to be within the boundary of the survey area (i.e., within the field of view of the mobile gas measurement device of the vehicle 24). We also consider drawing a sample from the distribution of wind directions and drawing a line through the candidate point Q in this direction. If this line intersects the path 74 of the vehicle 24 within the time interval $-T<t<T$, and the distance from the candidate point Q to the point of intersection with the path 74 is less than or equal to the estimated maximum distance $X_{max}$, then this is regarded as detectable by the mobile gas measurement device since the potential gas emission source at the candidate point Q would have been detected along the path 74. The quantity T sets the time interval during which it is expected to detect the gas coming from the candidate point Q at measurement point P. Theoretically, the time interval can be large, but it may not be reasonable to assume that the wind statistics remain unchanged for an extended period of time. In some embodiments, the wind direction measurements are taken during a time interval less than or equal to about 2 minutes, during which time interval a gas concentration is measured at the gas concentration measurement point P. More preferably, the time interval is in the range of 10 to 20 seconds.

Figure 10:
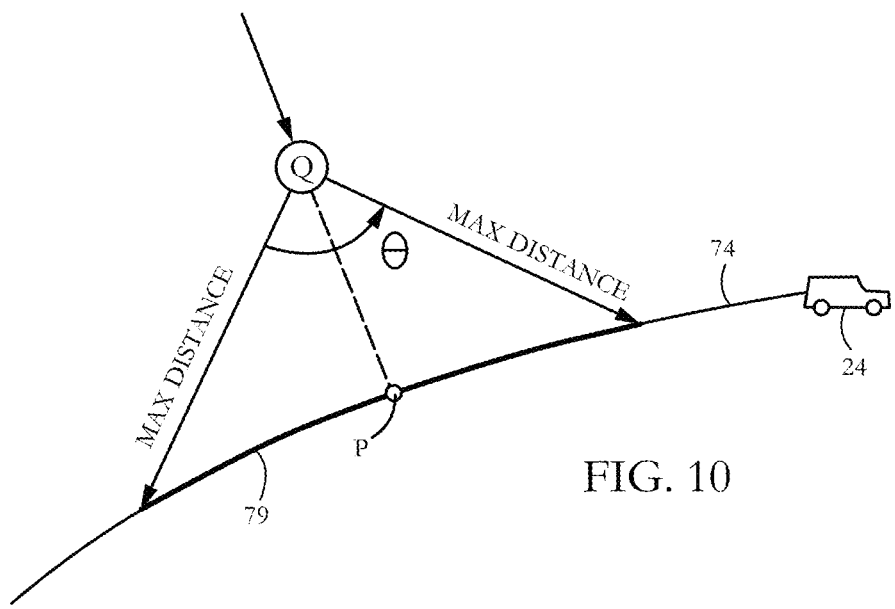
FIG. 10 is a schematic diagram of wind direction and a path of a mobile gas measurement device used to estimate a probability of detection of a gas leak from a potential gas leak source at one or more measurement points along the path according to some embodiments of the present invention.

FIG. 10 is a schematic diagram showing the estimation of a probability of detection at the measurement point P of a gas emission from a potential gas emission source at the candidate point Q, according to some embodiments of the present invention. The probability of detection at measurement point P is estimated according to an angle θ subtended by a segment 79 of the path 74 relative to the candidate point Q for the potential gas emission source. The path segment 79 is positioned within a distance of the candidate point Q that is less than or equal to the estimated maximum distance $X_{max}$. The probability of detection is preferably estimated according to a cumulative probability of wind directions with respect to the subtended angle θ. The cumulative probability of wind directions may be determined according to a representative wind direction (e.g., a mean, median, or mode of the wind direction measurements) and a wind direction variability (e.g., variance or standard deviation) calculated from the wind direction measurements.

The candidate point Q is deemed to be within the boundary of the survey area if the probability of successful detection of a potential gas leak source at the candidate point Q, over the distribution of wind directions, satisfies a probability condition. In some embodiments, the probability condition to be satisfied is an estimated probability of successful detection greater than or equal to a threshold value, typically set at 70%. In general, as the candidate point Q is moved a farther distance from the gas concentration measurement point P, the range of successful angles becomes smaller and the probability of success decreases, reaching a probability threshold at the boundary of the territory deemed to be within the survey area.

Figure 11:
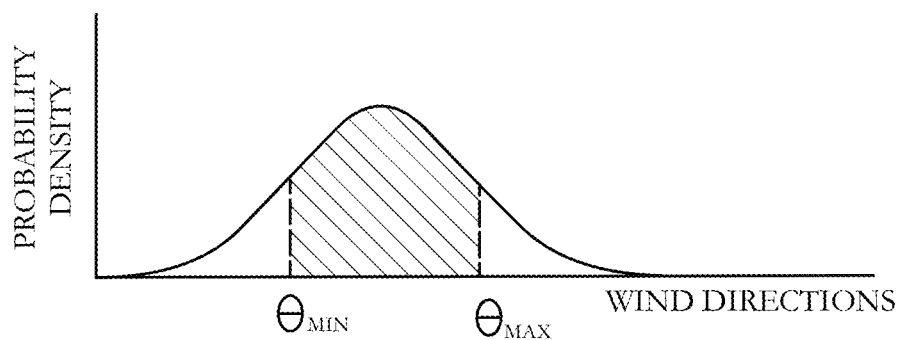
FIG. 11 is a graph of probability density vs. wind directions for estimating a probability of detection of a gas leak from a potential gas leak source according to some embodiments of the present invention.

FIG. 11 is a graph of probability density vs. wind directions for estimating a probability of detection of a gas leak from a potential gas leak source, according to some embodiments of the present invention. The area under the curve spans a range of possible angles θ for the successful detection of a potential gas leak from a candidate point. The probability density may be generated as a Gaussian or similar distribution from the calculated mean and standard deviation of the wind direction measurements in the area of the gas concentration measurement point P, FIG. 10. If the angle θ subtended by the path segment 79 relative to the candidate point Q encompasses a cumulative probability that is greater than equal to a threshold percentage (e.g., 70%, although the percentage may be adjusted to other values such as 50%, 60%, 67%, 75%, 80%, or 90% in some embodiments), and if the distance from the candidate point Q to the measurement point P is less than the estimated maximum distance $X_{max}$, then the candidate point Q is deemed to be within the survey area.

The above process is repeated as different measurement points along the path 74 are chosen and different candidate points are evaluated for the probability of successful detection of a potential gas leak source. The cumulative distribution of the wind direction function together with a root finding algorithm are useful for efficiently determining the boundary of the survey area. For example, referring again to FIG. 10, the root finding algorithm may consider candidate points along the line of mean wind direction starting at the estimated maximum distance $X_{max}$ from measurement point P, and iteratively (e.g. using a bisection or other method) moving closer to the measurement point P along the mean wind direction line until the angle θ subtended by the path segment 79 is sufficient to meet the probability threshold, as determined from the cumulative probability of wind directions over the subtended angle θ, FIG. 11. Referring again to FIG. 4, the survey area indicator 80 may be displayed on the map 70 as a colored "swath" adjoining the path 74 and extending in a substantially upwind direction from the path.

Figure 12:
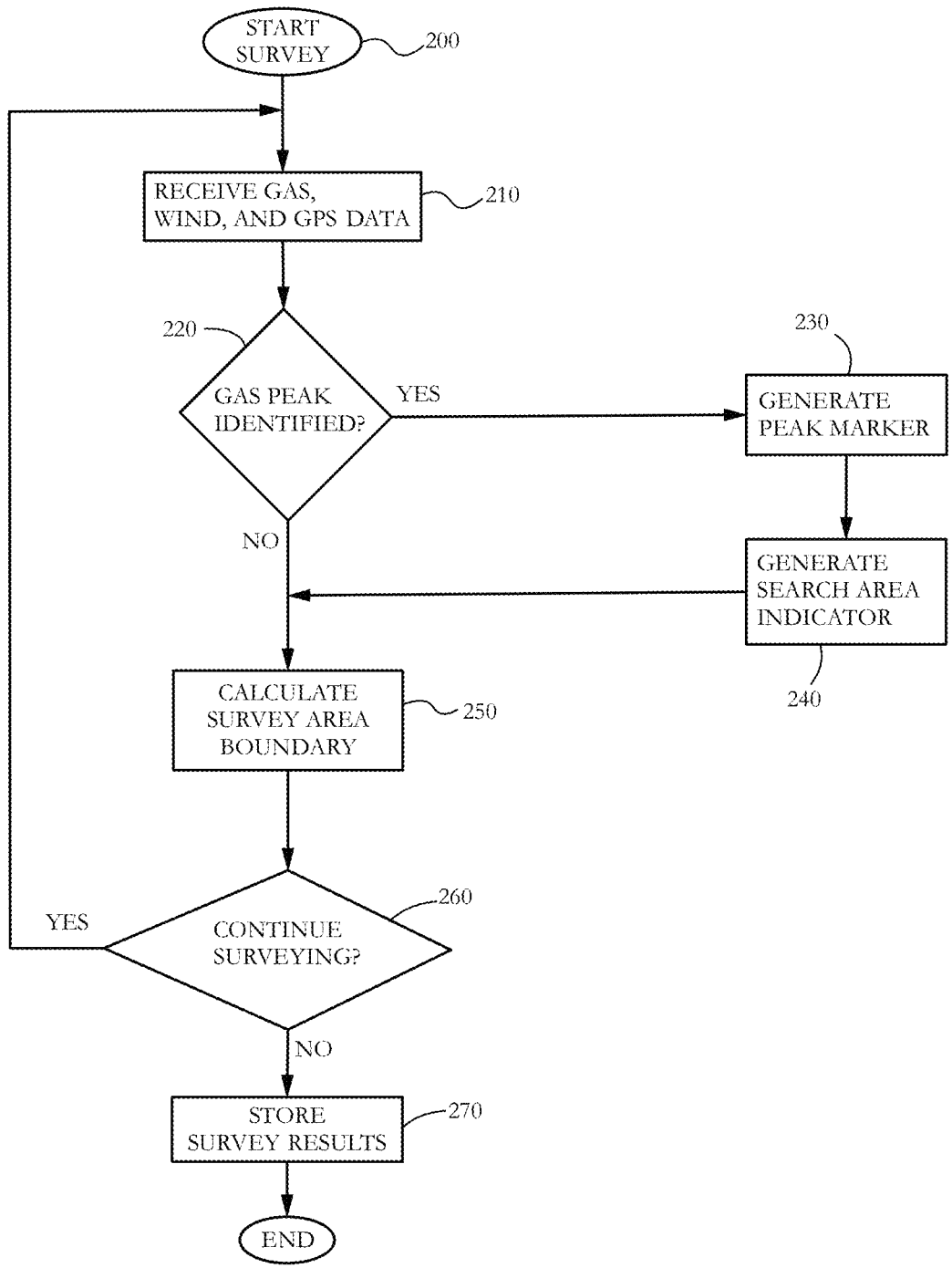
FIG. 12 is a flow chart showing steps for performing a gas leak survey according to some embodiments of the present invention.

FIG. 12 is a flow chart showing a sequence of steps to perform a gas leak survey according to some embodiments of the present invention. In step 200, the survey program is started, for example by an operator in the vehicle using a graphical user interface (GUI). The operator begins to drive the vehicle on a survey route while the GUI displays a street map (FIG. 4). Gas concentration measurements are preferably performed rapidly along the survey route (e.g., at a rate of 0.2 Hz or greater, more preferably 1 Hz or greater). This enables the practice of driving the vehicle at normal surface street speeds (e.g., 35 miles per hour) while accumulating useful data. The gas concentration is measured initially as a function of time, and is combined with the output of the GPS receiver in order to obtain the gas concentration as a function of distance or location. Interpolation can be used to sample the data on a regularly spaced collection of measurement points. The concentration of methane typically varies smoothly with position, for the most part being equal to the worldwide background level of 1.8 parts per million together with enhancements from large and relatively distant sources such as landfills and marshes.

In step 210, at least one processor (e.g. of a client device, server device, or a combination) receives data representative of measured gas concentrations, wind direction measurements, wind speed measurements, and GPS data. In decision block 220, it is determined if a peak in gas concentration is identified. A peak may be identified from a gas concentration measurement above a certain threshold (or within a certain range), or exceeding background levels by a certain amount, which may be predetermined or user-selected. In some embodiments, the gas concentration and GPS data are analyzed using a peak-location method, and then each identified peak is subsequently fit (using linear or nonlinear optimization) for center and width. The functional form used for this fitting step may be a Gaussian pulse, since a Gaussian is commonly the expected functional form taken by gas plumes propagating through the atmosphere.

If a peak in gas concentration is not identified, then the program proceeds to step 250. If a peak in gas concentration is identified, then a peak marker is generated in step 230. The peak marker may be displayed on the map as a user-selectable layer, as previously discussed with reference to FIG. 4. In step 240, a search area indicator is generated to indicate the likely location of a gas leak source corresponding to the identified peak in gas concentration. The search area indicator may be displayed on the map as a user-selectable layer, as shown in FIG. 4. In step 250, the survey area boundary is calculated, and a survey area indicator may be displayed on the map as a user-selectable layer (hatched region in FIG. 4). In decision step 260, it is determined if the operator wishes to continue surveying (e.g., by determining if the "Stop Survey" button has been selected). If yes, the survey program returns to step 210. If not, the survey results are stored in memory in step 270 (e.g., in the survey results 64 of FIG. 3), and the survey program ends.

Figure 13:
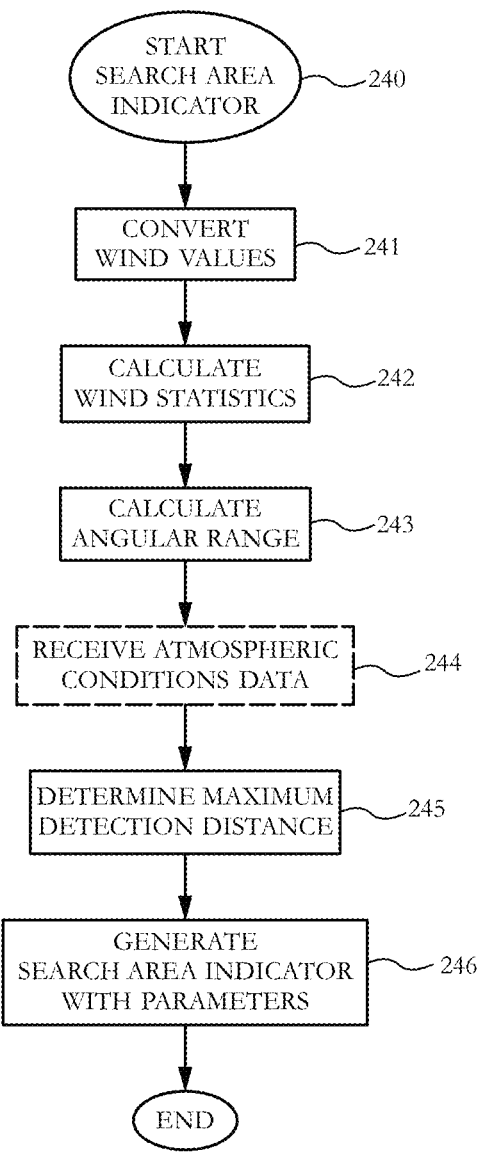
FIG. 13 is a flow chart showing steps for generating a search area indictor according to some embodiments of the present invention.

FIG. 13 is a flow chart showing a sequence of steps performed to generate a search area indicator according to some embodiments of the present invention. When a local enhancement in the gas concentration is detected, the likely direction and estimated distance to the potential gas leak source is preferably calculated from data representative of wind direction and wind speed measured during a time interval just prior to or during which the gas concentration was measured. The time interval is preferably fewer than 2 minutes, and more preferably in the range of 5 to 20 seconds. Calculating statistics from wind measurements may require some conversion if the measurements are made using sensors on a moving vehicle. A sonic anemometer is preferably used to measure wind along two perpendicular axes. Once the anemometer has been mounted to the vehicle, these axes are preferably fixed with respect to the vehicle. In step 241, wind speed and wind direction values that were measured relative to the vehicle are converted to wind speed and wind direction values relative to the ground by subtracting the velocity vector of the vehicle, as obtained from the GPS data. When the vehicle is stationary, GPS velocity may be ineffective for determining the orientation of the vehicle and wind direction, so it is preferable to use a compass (calibrated for true north vs. magnetic north) in addition to the anemometer.

In step 242, wind statistics are calculated from the converted wind values to provide the parameters for the search area indicator. The statistics include a representative wind direction that is preferably a mean, median, or mode of the wind direction measurements. The statistics also include a wind direction variability, such as a standard deviation or variance of the wind direction measurements. In step 243, an angular range of search directions, extending from the location of the gas concentration measurement point where the local enhancement was detected, is calculated according to the variability of the wind direction measurements. In optional step 244, atmospheric conditions data are received. Step 245 is determining a maximum detection distance value representative of the estimated maximum distance from the suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 246, the search area indicator is generated with the determined parameters, previously discussed with reference to FIG. 8.

Figure 14:
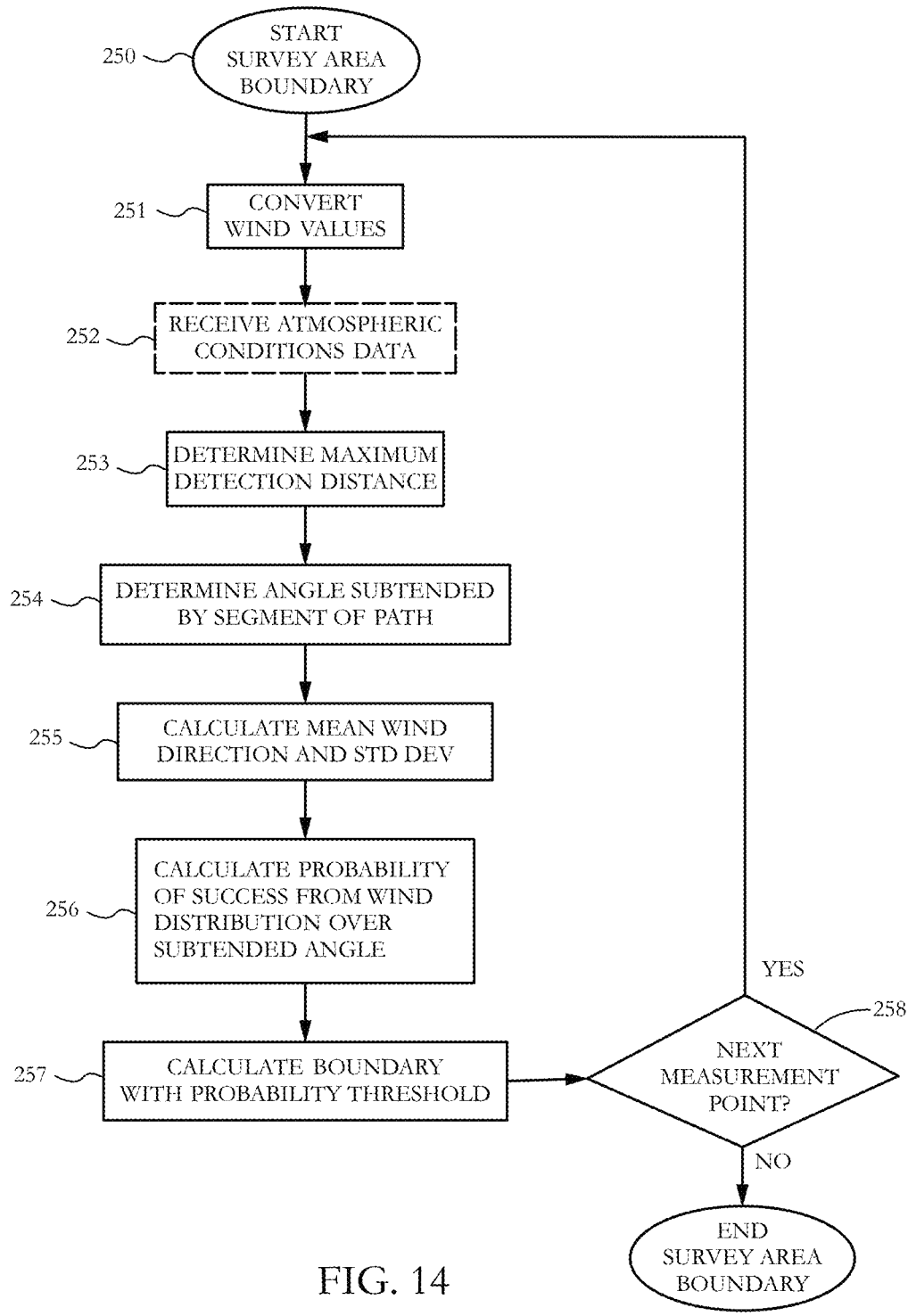
FIG. 14 is a flow chart showing steps for calculating a boundary of a survey area according to some embodiments of the present invention.

FIG. 14 is a flow chart showing a sequence of step performed to calculate a boundary of a survey area according to some embodiments of the present invention. In step 251, wind speed and wind direction values that were measured relative to the vehicle are converted to wind speed and wind direction values relative to the ground by subtracting the velocity vector of the vehicle, as previously described in step 241 above. In optional step 252, atmospheric conditions data are received. Step 253 is determining a maximum detection distance value representative of the estimated maximum distance from a suspected gas leak source at which a leak can be detected. In some embodiments, the maximum detection distance value is determined according to Equation (3) or Equation (4), and the data representative of wind speed and/or atmospheric stability conditions. Alternatively, the maximum detection distance value may be a predetermined number, a user-defined value, empirically determined from experiments, or a value obtained from a look-up table. In step 254, it is determined what angle θ is subtended by a segment of the path of the vehicle relative to the candidate point Q for the potential gas leak source. The path segment is positioned within a distance of the candidate point Q that is less than or equal to the estimated maximum distance.

In step 255, a representative wind direction (e.g., a mean, median, or mode of the wind direction measurements) and a wind direction variability (e.g., variance or standard deviation) are calculated from the wind direction measurements. In step 256, the probability of detection is estimated according to a cumulative probability of wind directions with respect to the subtended angle θ. In step 257, the survey area boundary is calculated with a probability threshold. For example, if the angle θ subtended by the path segment relative to the candidate point encompasses a percentage of possible wind vectors that is greater than equal to a threshold percentage (e.g., 70%,), and if the distance from the candidate point Q to the measurement point P is less than the estimated maximum distance $X_{max}$, then the candidate point Q is deemed to be within the survey area. In decision step 258, it is determined if the survey area boundary function is to continue with the next measurement point. If yes, steps 251-257 are repeated as different measurement points along the path are chosen and different candidate points are evaluated for the probability of successful detection of a potential gas leak source. If not, then the boundary function ends.

Figure 15:
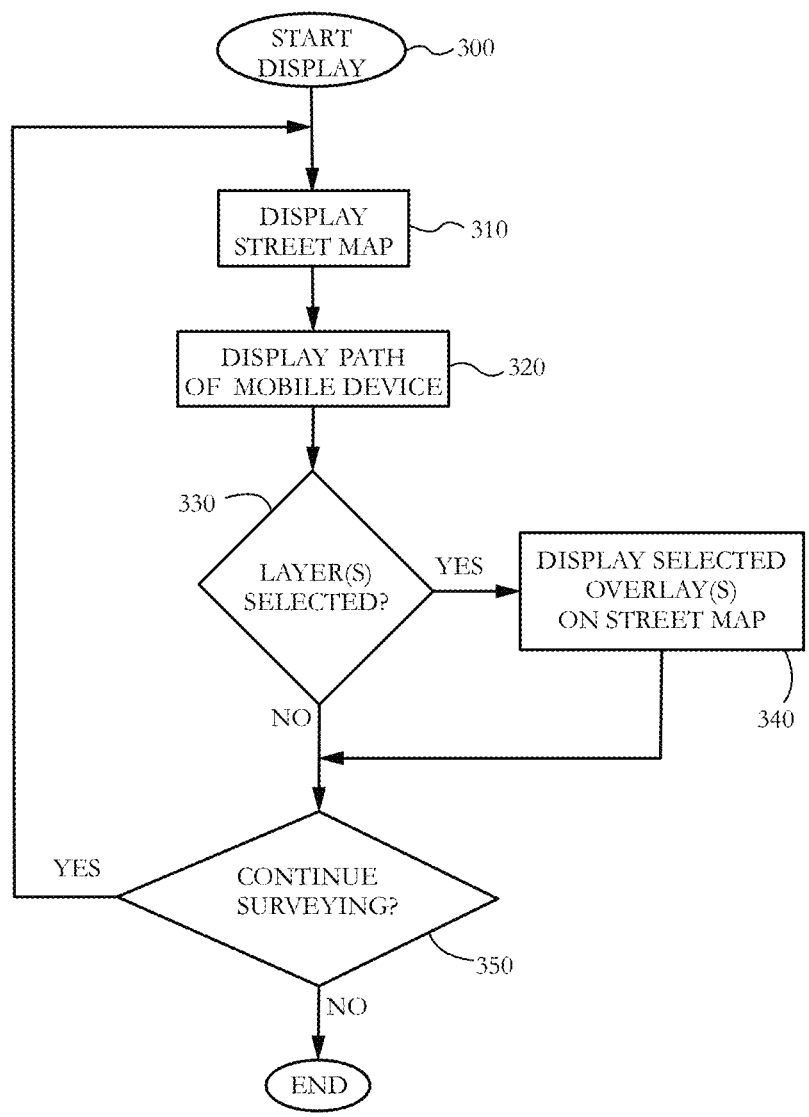
FIG. 15 is a flow chart showing steps for displaying layers overlaid or superimposed on a street map according to some embodiments of the present invention.

FIG. 15 is a flow chart showing steps for displaying layers overlaid or superimposed on a street map according to some embodiments of the present invention. In step 310, a street map is displayed, preferably on a GUI visible to the operator in the vehicle. In step 320, the path of the vehicle with the mobile gas measurement device is displayed on the map. Various elements displayed on the map are regarded as layers which may be turned on or off. In this example, the map controls window (FIG. 7) includes six user-selectable buttons named "Hide Peak Markers", "Hide Search Area Indicators", "Minimum Amplitude", "Hide Isotopic Analysis", "Hide Field of View", and "Hide Plat Outline". In decision step 330, it is determined if one or more of these layers is selected. If yes, the selected layer is displayed overlaid or superimposed on the street map in step 340. If not, it is determined if the survey is to continue. If yes, display steps 310-350 are repeated. If not, the display options may end.

2-D Surface Probability Distributions (Heat Maps), Multi-Run Data Collection and Analysis In some embodiments, gas emissions and/or atmospheric condition data collected and analyzed as described above may be used to generate 2-D surface distributions of a number of parameters, such as 2-D maps of the probability that a gas emission source is located at each location (pixel) along the map, or of the probability that a gas emission source would have been detected had it been present at each location along the map. Such 2-D maps may be updated using data collected on multiple measurement runs performed along the same path or different paths.

Figure 19:
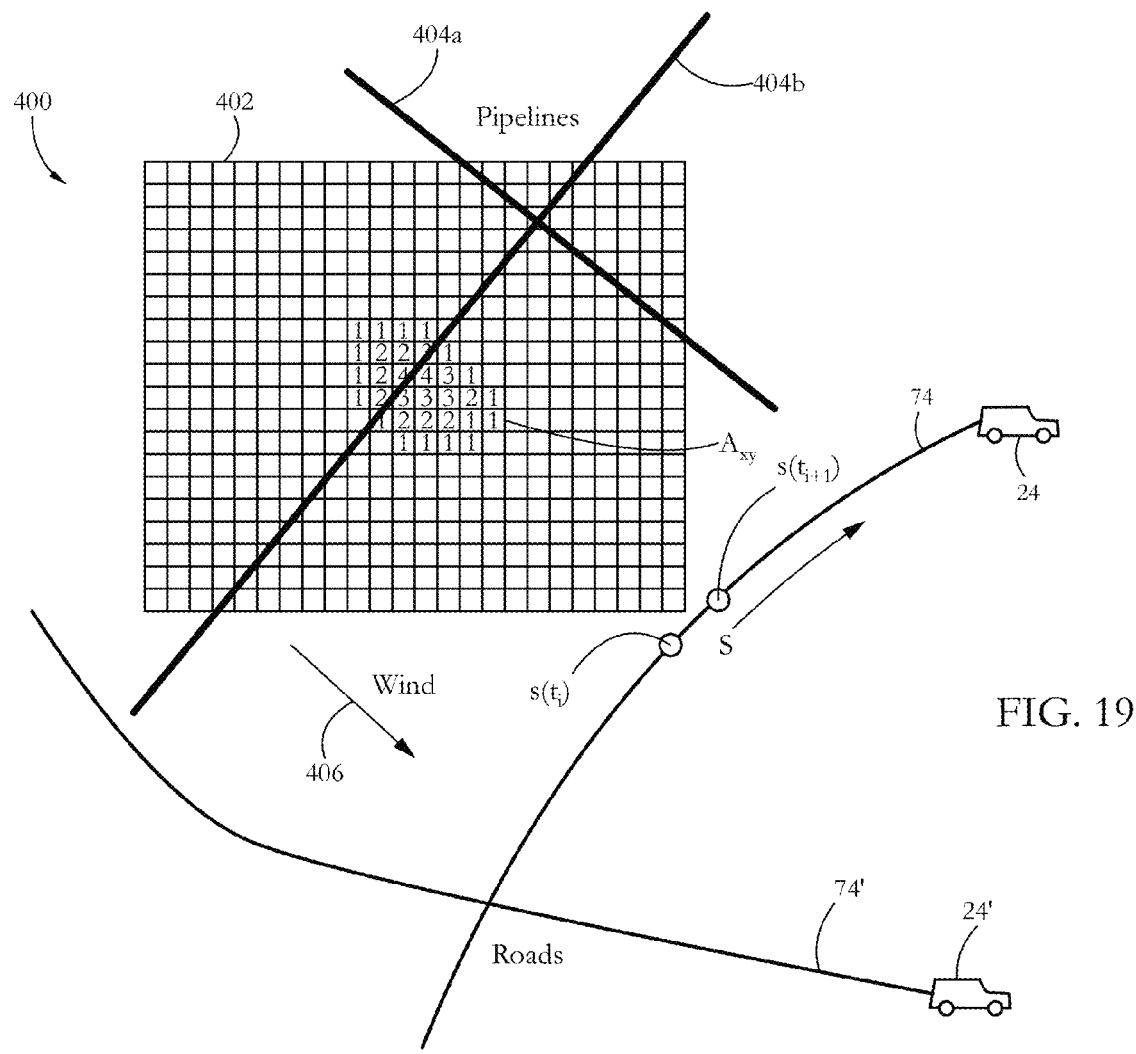
FIG. 19 illustrates an exemplary 2-D surface map including an array of pixels (locations) each having an associated parameter value, according to some embodiments of the present invention.

FIG. 19 illustrates an exemplary 2-D surface map 400 including an array of pixels (locations) 402, each having an associated parameter value, according to some embodiments of the present invention. In some embodiments, each location 402 may represent a square having a side length on the order of tens of meters, meters, or tens of cm. An associated parameter value may be an absolute or relative probability that a gas emission source is located at the given location, among others. A number of such probabilities are represented in FIG. 19 by index values 0-4, with zero values shown as blank, 0 value representing a lower probability, and 4 representing a higher probability. Continuously-variable parameters may be used instead of, and/or in conjunction with discretely-varying indexes as illustrated in FIG. 19. In some embodiments, the associated parameter value may be a surveyed area Boolean (yes/no) value indicating whether an emissions source at the given location having a given emission flux would have been detected in one or more previous measurement runs, had the source been present at that location.

Two measurements paths 74, 74' represent the paths taken by measurement vehicles 24, 24' on separate measurement runs, which may be performed on different days and under different atmospheric conditions. In some embodiments, separate measurement runs may be performed along a single path under different atmospheric conditions. The general wind direction corresponding to a measurement run performed along measurement path 74 is shown at 406. To reduce display clutter, 2-D surface map 400 is shown in FIG. 19 only along part of the area over which it may extend; it is understood that 2-D surface map 400 may extend along a larger area than explicitly shown in FIG. 19.

Figure 20:
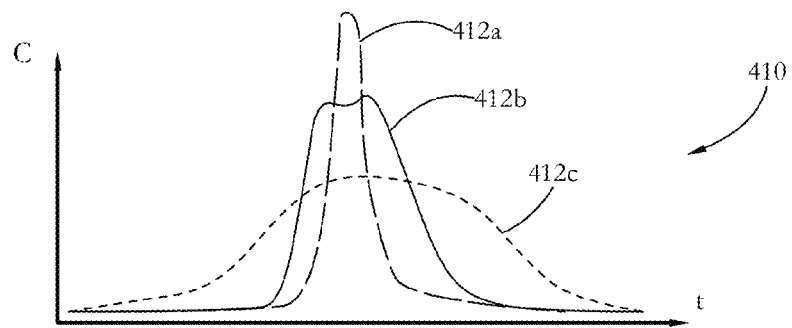
FIG. 20 shows three exemplary variations of detected concentration with time for three measurement runs performed along a measurement path shown in FIG. 19, according to some embodiments of the present invention.

FIG. 20 shows three exemplary variations of detected concentration with time 410 for three measurement runs performed along the measurement path 74 shown in FIG. 19, according to some embodiments of the present invention. Three detected plume events are represented by peaks 412a-c; the three detected plume events may represent gas plumes originating at a common location upwind from measurement path 74, for example in an area represented by probability indexes of 4 in FIG. 19. Peaks 412a-c may correspond to different atmospheric conditions, for example to different wind speeds and/or directions present at the different times of different runs. Peaks 412a-c thus may be characterized by different peak amplitudes and widths even if all three plume events characterize the same source location and emission flux. For example, a narrower peak 412a may correspond to a measurement run during strong wind conditions, while a broader peak 412c may correspond to a measurement run during weak wind conditions. In some embodiments, different peaks such as peaks 412a-c may represent detections of the same gas plume along different measurement paths.

Figure 21:
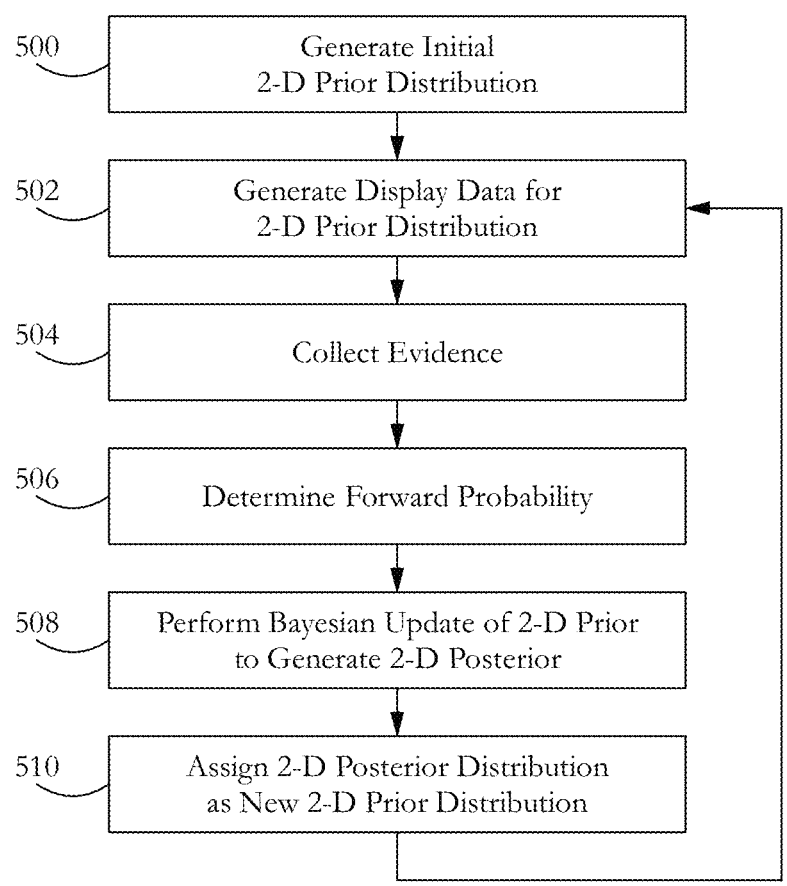
FIG. 21 is a flowchart illustrating generally a number of steps performed in an exemplary Bayesian update method according to some embodiments of the present invention.

FIG. 21 is a flowchart illustrating generally a number of steps performed in an exemplary Bayesian update method according to some embodiments of the present invention. In a step 500, an initial 2-D prior spatial distribution of a parameter of interest is determined. According to some embodiments, such parameters of interest may include: a probability (e.g. a maximum probability) that a gas emissions source of a given minimum size/flux is present at a given location; the maximum flux of a source likely to be present at a given location; whether a given location has been surveyed to a specified confidence level; a relative likelihood that a source is present at one location relative to another; a probability that at least one source of a given flux is present at a given location; and a sensitivity of measurements to a hypothetical source or sources of a given flux or fluxes at a given location (sensitivity may be determined as an average flux upper limit, at a given confidence level, that would be obtained for an ensemble of identical experiments when no sources are present). Other parameters of interest may be defined in some embodiments. In some embodiments, statistics or other evaluation data may be computed based on the 2-D spatial distribution(s) of parameters of interest. For example, the total number of leaks detected in a given region can be quantified by a local maximum area-based analysis of a probability map. Such an analysis may include identifying local maxima separated by a pre-defined minimum distance (e.g. 100 ft), and/or performing simulations for closely-spaced peaks to determine whether the measured data is more consistent with a single-source or multi-source hypothesis. Other evaluation parameters determined for the 2-D prior spatial distribution may include confidence levels and robustness estimates for the distribution or part of the distribution.

The initial 2-D prior spatial distribution may be spatially uniform or heterogeneous, and temporally uniform or heterogeneous. For example, a surveyed area distribution may be initialized to zero before any measurements are performed. A source probability distribution may be initialized to zero, or to higher values along known gas distribution infrastructure (e.g. pipeline and gas service) locations as identified from gas company records/plats and lower values elsewhere. The values selected along gas distribution infrastructure may be further selected according to the condition (e.g. age, reliability records/expectations) and expected emission factors for different types of infrastructure. In some embodiments, the distribution may be temporally heterogeneous, to reflect changes in emission rates and/or probabilities with time. For example, gas pipelines may have higher pressures in the winter than the summer, and may have different pressures at different times of the day or the week. Surface permeability may vary with temperature and thus with seasons and the time of day, for example as cracks in asphalt open and close with variations in temperature. Some gas distribution systems use relief valves that release gas at determinable times. And some sources of natural gas resulting from incomplete combustion (e.g. laundromats, restaurants, and buses running on compressed natural gas) have emission rates that vary with time and/or space.

In a step 502, display data is generated for displaying the 2-D prior spatial distribution to a user. Such display data is transmitted to a display device, which displays to the user a graphical representation of the 2-D prior spatial distribution. The graphical representation may be a color-coded or other type of heat-map illustrating the 2-D prior spatial distribution and other geospatially-referenced features, as illustrated for example in FIGS. 4-7 and 19.

In a step 504, evidence is collected along a 1-D path (or at multiple locations) as described above, and from external sources. For example, atmospheric condition data may be collected from an outside station or service. Collected evidence may include raw measurements, as well as data derived from raw measurements, such as a Boolean flag indicating whether a plume was detected at a given location, and/or the peak size and width of a plume detected at a given location. In some embodiments, examples of collected evidence include one or more of the following: geospatial (e.g. GPS) position and time; primary gas concentration taken at one or more vertical positions with respect to the vehicle; processed gas concentration indicating an observed plume; secondary tracer gas concentration; wind direction and speed; plume location, peak and width; emission rate; estimated distance and/or direction to a source; estimated source size.

In a step 506, a forward probability of detecting evidence given a state on the 2-D surface is determined. In some embodiments, the forward probability may be determined using an atmospheric transport model to transform a real or hypothetical emissions source characterized by a location and flux into observed concentrations at different locations, or into probabilities of being detected by measurements performed along the 1-D path. The model used to determine the forward probability may be a physical (theoretical) and/or empirically-determined model. Such an empirical model may rely on prior experimental measurements. Empirical data (e.g. wind direction and wind speed data measured in real time on the vehicle) may also be used to modify parameters in a theoretical model. The forward probability calculation for a 2-D spatial distribution for one quantity may also be constrained by a previously-determined 2-D spatial distribution for another quantity; for example, a previously-determined 2-D distribution of likely source locations may be used to constrain calculations of a 2-D spatial distribution of source fluxes. In some embodiments, if additional evidence is available, such as estimates of leak size or distance to leak, such evidence can be incorporated into the forward probability calculation.

In some embodiments, multiple forward probabilities may be calculated, and differences between forward probabilities calculated with different models or under different assumptions may be used as a measure of data quality and/or as criteria for data selection. Multiple spatial distributions calculated with different forward likelihood kernels may be used in combination to reveal other information about possible sources, such as the relative likelihood that the source is localized (point-like) or extended spatially, or is of constant or time-varying flux. In some embodiments, a forward probability density may be factorized as a product of quasi-independent functions of single variables, as described below.

In a step 508, a Bayesian update is performed using the computed forward probabilities to generate a 2-D posterior spatial distribution from the 2-D prior spatial distribution as described below. In a step 510, the 2-D posterior spatial distribution is assigned to be the new prior spatial distribution, and the process returns to step 502 and proceeds for one or more subsequence rounds of data display, collection and update.

Suitable Bayesian update methods are described below for a number of exemplary 2-D spatial distributions and associated algorithms. The algorithms described below can be broadly divided into two categories: those that characterize detected leaks, or make inferences about the properties of unknown sources of gas such as their location or flux, based on one or more positive indications that at least one source is present, and those that assess the sensitivity to undetected leaks, or the probability that a source with given properties would have been detected if it had been present, when no positive indications were found or no concentration data is considered at all.

Leak-locating algorithms generally use as input a minimum of one positive indication, while those that assess sensitivity do not require positive detections. A positive indication may be taken to mean that an elevated concentration of the gas, consistent with the mobile system having traversed a plume of the gas of interest, was detected above the ambient background. In some embodiments, whether such detection has occurred is determined using an automated spatial-scale and threshold analysis. Such an analysis may include, but is not limited to, a determination of the spatial extent (width) of the gas plume along the trajectory of the mobile system (see e.g. the different widths illustrated in FIG. 20), the maximum concentration of the gas above ambient (see e.g. the different peak heights illustrated in FIG. 20), and the calculation of parameters describing the shape of the concentration curve (such as a moment analysis, or the variability of the concentration from one point to the next). For example, a nearby source is likely to result in a relatively tall, sharp peak having a well-defined shape that varies monotonically up and down), while a more distant source is likely to result in a relatively short, wide peak having a bumpier shape. All or some of the outputs of such an analysis may be used by the algorithms that characterize the unknown gas source giving rise to the positive indication (s).

Figure 22:
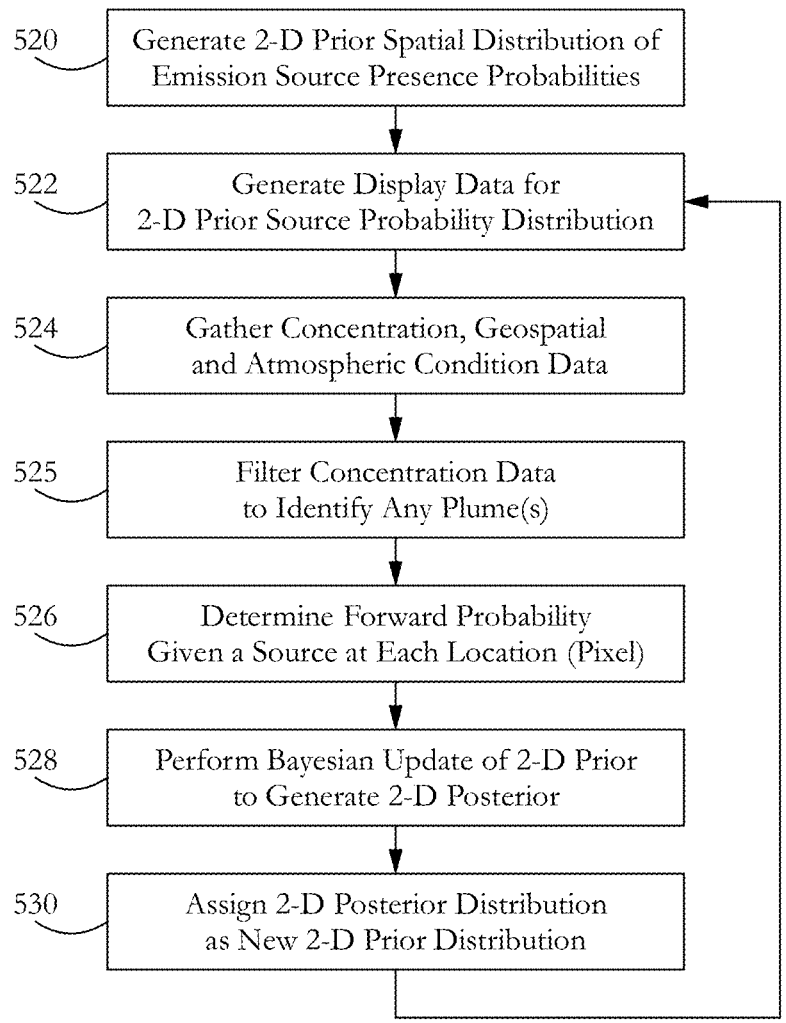
FIG. 22 shows an exemplary sequence of steps performed in a Bayesian update of an emission-characterization 2-D spatial distribution according to some embodiments of the present invention.

FIG. 22 shows an exemplary sequence of steps performed in a Bayesian update of an emission-characterization 2-D spatial distribution according to some embodiments of the present invention. In a step 520, a 2-D prior spatial distribution of emission source presence probabilities is generated as described above. In a step 522, display data is generated for displaying the 2-D prior spatial distribution. In a step 524, gas concentration, geospatial location, and atmospheric condition data are collected in a measurement run as described above. In a step 525, the concentration data is filtered to identify any plumes; non-plume concentration data is not used in subsequent update steps. In a step 526, the forward probability of detecting a plume at all (i.e. a T/F) and/or a plume having given characteristics (e.g. given peak and/or width values) given a source at each location are determined. In some embodiments, the probability of interest is a relative rather than absolute probability, allowing comparisons between locations, and in particular comparisons to data from a known source. In some embodiments, a fixed total probability is assigned to each positive event, i.e. each positive detection event is weighted the same as all others. In a step 528, a Bayesian update is performed to determine a posterior 2-D spatial distribution of emission source probabilities. In a step 530, the posterior 2-D spatial distribution is assigned to be the new prior, and the process above is repeated.

Figure 23:
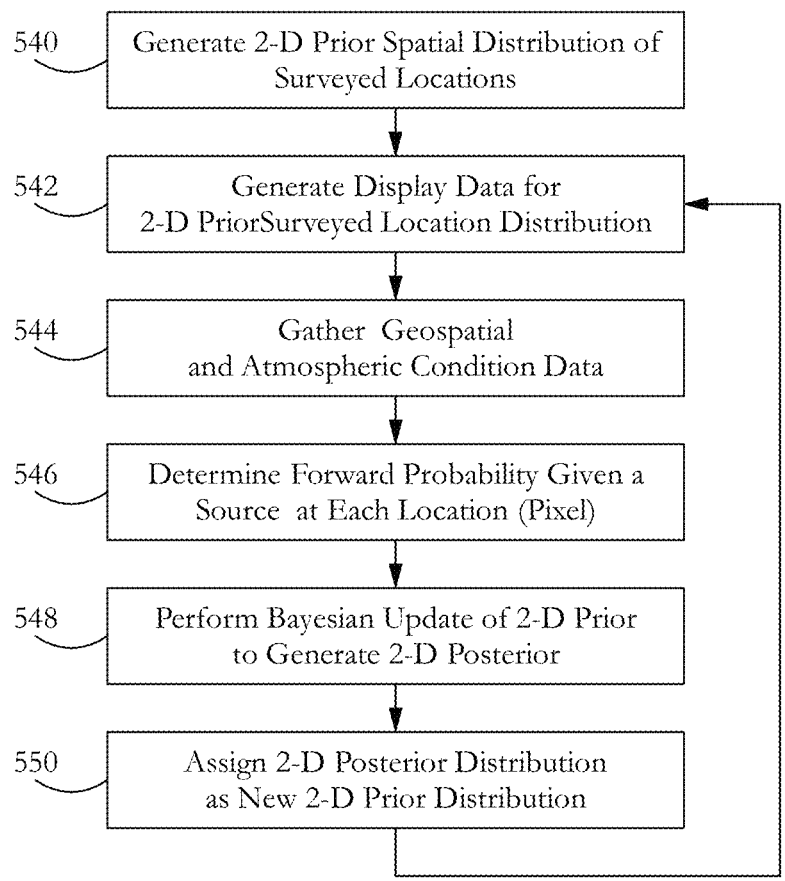
FIG. 23 shows an exemplary sequence of steps performed in a Bayesian update of a sensitivity 2-D spatial distribution according to some embodiments of the present invention.

FIG. 23 shows an exemplary sequence of steps performed in a Bayesian update of a sensitivity 2-D spatial distribution according to some embodiments of the present invention. In a step 540, a 2-D prior spatial distribution of surveyed locations is generated as described above. In a step 542, display data is generated for displaying the 2-D prior spatial distribution. In a step 544, geospatial location and atmospheric condition data are collected in a measurement run as described above. In a step 546, the forward probability of detection given a source at each location is determined. The probability of detection may be the probability of detecting a source as described above, and/or the probability of detecting a plume having given characteristics.

In a step 548, a Bayesian update is performed to determine a posterior 2-D spatial distribution of surveyed locations. In particular, a posterior probability of missing detection of a potential gas source situated at a given location is determined according to a product of: i. a prior probability of missing detection of the potential gas source situated at the given location, and ii. a probability of missing detection of the potential gas source situated at the given location during the current measurement run. In a step 550, the posterior 2-D spatial distribution is assigned to be the new prior, and the process above is repeated.

Observations of the same gas source across multiple passes are tied together by the fact that the propagation of gaseous emissions in the atmosphere is governed by atmospheric transport phenomena; i.e., the emissions are carried horizontally by the wind, as well as being dispersed by diffusion and convective processes. Thus, on a trajectory that approaches close to a gas source, the emissions plume may be highly peaked, whereas a track further downwind will likely show a reduced, broader plume, as illustrated in FIG. 20. Characterization algorithms can take advantage of observables that are diagnostic of the distance and position of the source. Even if the measurements from a single pass through an emissions plume is not very restrictive of the properties sought, successive measurements, when combined intelligently with those made before, may be used improve our knowledge of the source, such as its location and/or flux.

Combining successive observations is facilitated by encoding the information from each positive indication, and in some cases measurements consistent with no plumes being detected, into a probability distribution describing the relative likelihood for each hypothesis—as parameterized by the source properties we seek to estimate—to have resulted in the observation made. The resulting probability distribution is then modified appropriately by successive observations and Bayesian updating.

In some embodiments, a forward probability distribution is generated using physical model (theoretical) and/or likelihood factorization (empirical) approaches. A physical model as described above may use use input from measurements of atmospheric transport quantities on the vehicle to adjust the model as measurements are made. The physical model can use as validation experiments performed as described below in the likelihood factorization approach. In a likelihood factorization approach, measurements of known gas sources under a number of different conditions may be used to deduce the shape of the forward probability distribution for each observable as a function of the source property one seeks to measure, such as its location relative to the observer or its flux. The probability distributions may also be functions of one or more variables related to atmospheric conditions. Optionally, in cases where the amount of forward data is insufficient to precisely determine the functional form of the distribution with respect to a certain parameter, a theoretically-motivated functional form for the dependence on that parameter may be chosen, guided by the available data. The probability distributions may be tuned, and the resulting performance of the algorithm tested, on independent data. One may assign a probability to a given hypothesis to have resulted in a given measurement by taking the product of the probabilities to have seen the particular value measured for each observable described by the empirically-determined probability distributions. Optionally, the PDFs for individual observables may have weights that are functions of the parameters of the transport model or other variables. As one example of likelihood factorization, one may factorize a spatial dependence of a probability distribution as a product of purely-radial function (e.g. an exponential declining with distance from source) and a purely-angular function (e.g. a function having a peak at a representative wind direction angle. As another example of likelihood factorization, a likelihood function may be taken to be a product of a function of plume width and a function of plume shape bumpiness; even if the two functions are not in fact completely independent of each other, using the product of the two may allow simplifying the processing needed to generate an overall forward probability distribution.

In regions where no positive indications are found, it may be desirable to rule out that sources are present. The extent to which this can be accomplished for a given point in space depends on the efficiency with which the mobile system can detect sources, and the amount of exposure the system has to that location as determined by the movement of the atmosphere. The detection efficiency is a function of the downwind distance from the source to the detector, the flux of the source, the degree of atmospheric instability, and the amount of time the gas has propagated since emerging into the atmosphere.

The ability to rule out small leaks is maximal closest to the trajectory of the mobile system, and decreases farther away. Detection sensitivity may be expressed as an average flux upper limit, at a chosen confidence level, that would be obtained for an ensemble of similar collections of observations in the case that no source is actually present. The ingredients for a calculation of such a flux upper limit for a given point in space are the efficiency to detect gas sources as a function source flux, and the exposure of the system to gas emitted at that location. Both the efficiency and the exposure are strong functions of atmospheric stability and wind conditions. However, one can measure both quantities using data collected for known sources, as described above.

In some embodiments, multiple measurement runs performed on the same vehicle path or different vehicle paths may be used generate and/or update a 2-D spatial distribution. In particular, the understanding of a given map of potential leaks can be updated given a 1-D path of observations through the 2-D surface of potential leaks. In some embodiments, the updated likelihood can be calculated from each finite line-segment, so that paths can be added to the calculation without having to recalculate the entire spatial distribution. It may also be desirable that the probabilities be absolute, to facilitate interpreting directly the pixel values themselves.

Figure 24:
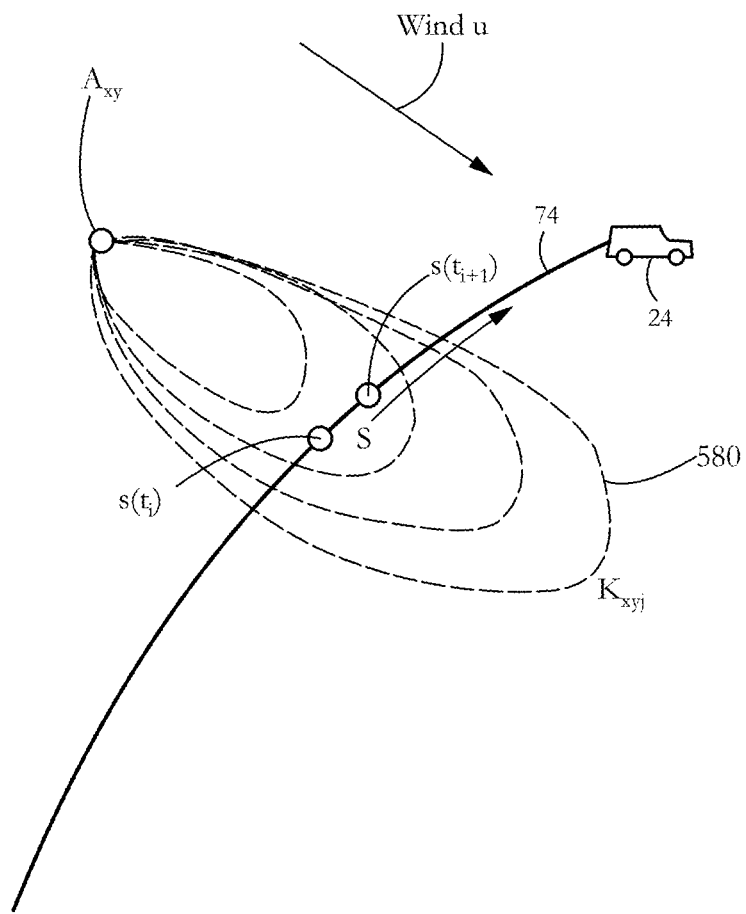
FIG. 24 illustrates several areas defined by corresponding plume detection likelihood intervals determined for a source location according to a forward probability kernel according to some embodiments of the present invention.

A Bayesian construct can be used to perform the update as described below with reference to FIG. 24. Consider a given pixel (location) $A_{xy}$ on the surface of interest, illustrated in FIG. 24. Further consider a path 74 parameterized as s(t), that lies on a surface parameterized by position (x, y). Measurements made along the path may include concentration, position, and measurements of real-time atmospheric transport properties. In principle, one could construct a complete Bayesian inference for all the pixels in the system for each single piece of evidence collected on the path s. However, this is a computationally intensive problem unless one assumes that there is just one source in the system. A single-source assumption leads to excellent localization properties, in which every plume detection leads to further localization as the understanding of the most likely location of the source is improved.

In some embodiments, each pixel is treated independently of other pixels. In other embodiments, values at one pixel may be used to determine values at adjacent pixels. Each approach is described in further detail below.

This multi-dimensional problem can be simplified significantly by applying each piece of evidence directly and independently at each pixel $A_{xy}$. In other words, each pixel may have a separate and distinct hypothesis to test: 1) is there a source, or 2) is there no source, at $A_{xy}$? In some embodiments, the probability of these hypotheses at each pixel may be assumed to be independent of the probabilities at other pixels. Such an assumption means that non-zero probabilities in other pixels do not influence the impact of evidence, and thus the evidence has maximal effect on the probability of a source in this pixel. Such an assumption thus leads to a calculation of a maximum probability of a source in a given pixel, assuming that the only source allowed for each piece of evidence is a source at this pixel. For the calculation of the adjacent pixel for that same piece of evidence, one may assume that the only source in the region is at this new location, and that no source is present at the original pixel. Enforcing independence between nearby pixels leads to a worst-case scenario for the probability of a source located at that pixel—the actual probability of one or more sources located at that location is always lower than or equal to the worst-case value. Because the probabilities generated for each pixel in this manner are maxima, they may be different from actual source probabilities.

In some embodiments, the results from adjacent pixels may be combined by assuming independence between the two pixels as a worst-case scenario, which means that the maximum probability of one or more sources in the combined area is the maximum probability of one or more sources in pixel #1 or pixel #2. For fully independent pixels, one can calculate this combined probability using the probability calculus described below. If the pixels are not independent of each other, as for two adjacent tiny (0.01 m²) pixels, the maximum probability of the combined pixel is simply the maximum of the two pixel probability. Again, OR-ing the two pixels is a worst case scenario, since that always leads to a larger value for the probability.

The inter-pixel interaction question can be stated as follows: if the probability of finding a leak in a given pixel is $P_1$, how does one add the probability from an adjacent pixel $P_2$? Restated, what is the likelihood of finding a source in pixel 1 OR pixel 2? This is equivalent to calculating the likelihood of finding no source in pixel 1 AND pixel 2, and then subtracting that result from unity. The 'AND' operation means that the probabilities multiply, so the probability of finding no source in either pixel is:

$$N_{12}=(1-P_1)(1-P_2)=1-P_1-P_2+P_1P_2 \quad [5a]$$

The probability of finding a source in either 1 or 2 is:

$$P_{12}=1-N_{12}=1-(1-P_1)(1-P_2)=P_1+P_2-P_1P_2 \quad [5b]$$

We may generalize these expressions to integration over M pixels:

$$N_{1\ldots M}=\Pi_{k=1}^{M}(1-P_k); P_{1\ldots M}=1-N_{1\ldots M} \quad [5c]$$

Such a method leads to pools of near unity maximum probability after the accumulation of identical T (True) evidence at the same location and wind conditions. The pools are approximately the size of the back-propagated plume. Note that even in this situation, every T has one (and likely many more) adjacent F (False) evidence, which will keep the pool from spreading too far. Such a pool does not mean that there are multiple sources. Such a method determines the maximum probability of finding at least one source within given contiguous area, and the resulting maps should be interpreted using the calculus of probability described above, i.e., as identifying the maximum probability of at least one source in the given region, and not by adding probabilities of neighboring pixels directly.

A 2-D spatial distribution generated by considering inter-pixel interactions as described above may be used in both characterization and sensitivity methods. In a characterization example, inter-pixel interactions may be used to determine the maximum probability of a source of a given size at a given location. Such a method may use both True and False evidence collected on the 1-D path. A cleared-area map may be generated by setting a threshold value for the worst-case probability of a source: such a map identifies the areas where the worst-case probability of a source is below the threshold. As noted above, combining pixels into larger areas using the probability calculus described above leads to a value which is a maximum probability of a source located in a given region.

In a sensitivity example, inter-pixel interactions may be used to determine the areas that have been surveyed for sources of a given size. Such a method may apply False evidence for all points on the 1-D measurement path, even if some evidence is actually true. The resulting probability represents the worst case scenario for not detecting an actual source of a given size at a given location. In other words, a value of 0.1 means that a source located here would be detected at least 9 out of 10 times. Combining pixels may be accomplished as described above. Expressing this result as a ratio of the prior allows mapping areas with substantially improved odds of detecting a leak.

Even if the quantity calculated is a maximum probability of a source, the calculation provides localization information. Non-detection events (i.e., F) lead to localization, because they reduce the probability of finding sources in the pixels that contribute to the event via the action of atmospheric transport. This formalism is especially useful in determining where no leaks are present (cleared areas) in a quantitative fashion—reduction of the source probabilities from the prior is accomplished via the accumulation of false plume readings. Sufficient passes of clean (F) readings with a well-defined wind transport allow reducing the source presence probabilities below a level corresponding to having surveyed and cleared an area.

An exemplary Bayesian update process may be better understood by considering the determination of the posterior probability that at least one source of gas with flux f is present in pixel $A_{xy}$, given an initial probability map of leaks ($P_{xy}$) and given evidence of plume identification (either T or F).

Using Bayes' theorem, we may write the posterior probability in the following manner:

$$p(H_{xy} | E_j) \equiv P'(H_{xy}) = p'_{xy} = \frac{p(E_j | H_{xy})\rho_{xy}}{p(E_j)} \quad [6]$$

where the left-hand term $p(H_{xy}|E_j) \equiv \rho_{xy}'$ is the posterior probability of the hypothesis, $H_{xy}$, that a source with flux greater than f located in the pixel at (x,y), $\rho_{xy}$ is the prior probability, $p(E_j)$ is the probability of the evidence $E_j$ given all possible hypotheses, and $p(E_j|H_{xy})$ is the modified probability of observing $E_j$ given $H_{xy}$. In this single pixel formalism, there are just two hypotheses to test at each pixel; i.e., whether or not there is a source at this location.

To determine $p(E_j)$ and $p(E_j|H_{xy})$, we use a forward likelihood kernel to calculate the likelihood of observing evidence $E_j$ given wind transport function $\Theta_j$. This probability kernel $K_{xyj}$ quantifies the likelihood of measuring a plume at location $s_j$ given wind transport $\Theta_j$ and a source at location (x,y). FIG. 24 illustrates graphically a number of area boundaries 580 determined using such a forward probability kernel. The area boundaries 580 are defined by different likelihood intervals.

The four probabilities $p(E_j|H_{xy})$ are:

$$P(T_j|S_{xy}); P(T_j|\overline{S_{xy}}); p(F_j|S_{xy}); p(F_j|\overline{S_{xy}}) \quad [7]$$

These probabilities depend on distance between the pixel and the evidence location, the direction relative to the possible wind directions, and the atmospheric stability class, and are captured in K. In some embodiments, K behaves such that $p(T_j|S_{xy}) \geq p(T_j|\overline{S_{xy}})$ and $p(F_j|S_{xy}) \leq p(F_j|\overline{S_{xy}})$. At great distance, or for angles that are far from the measured distribution of wind directions, $p(T_j|S_{xy}) = p(T_j|\overline{S_{xy}})$ and $p(F_j|S_{xy}) = p(F_j|\overline{S_{xy}})$. According to Bayes theorem, in this situation, the posterior probability is the same as the prior probability because the evidence cannot distinguish the two hypotheses.

Figure 25:
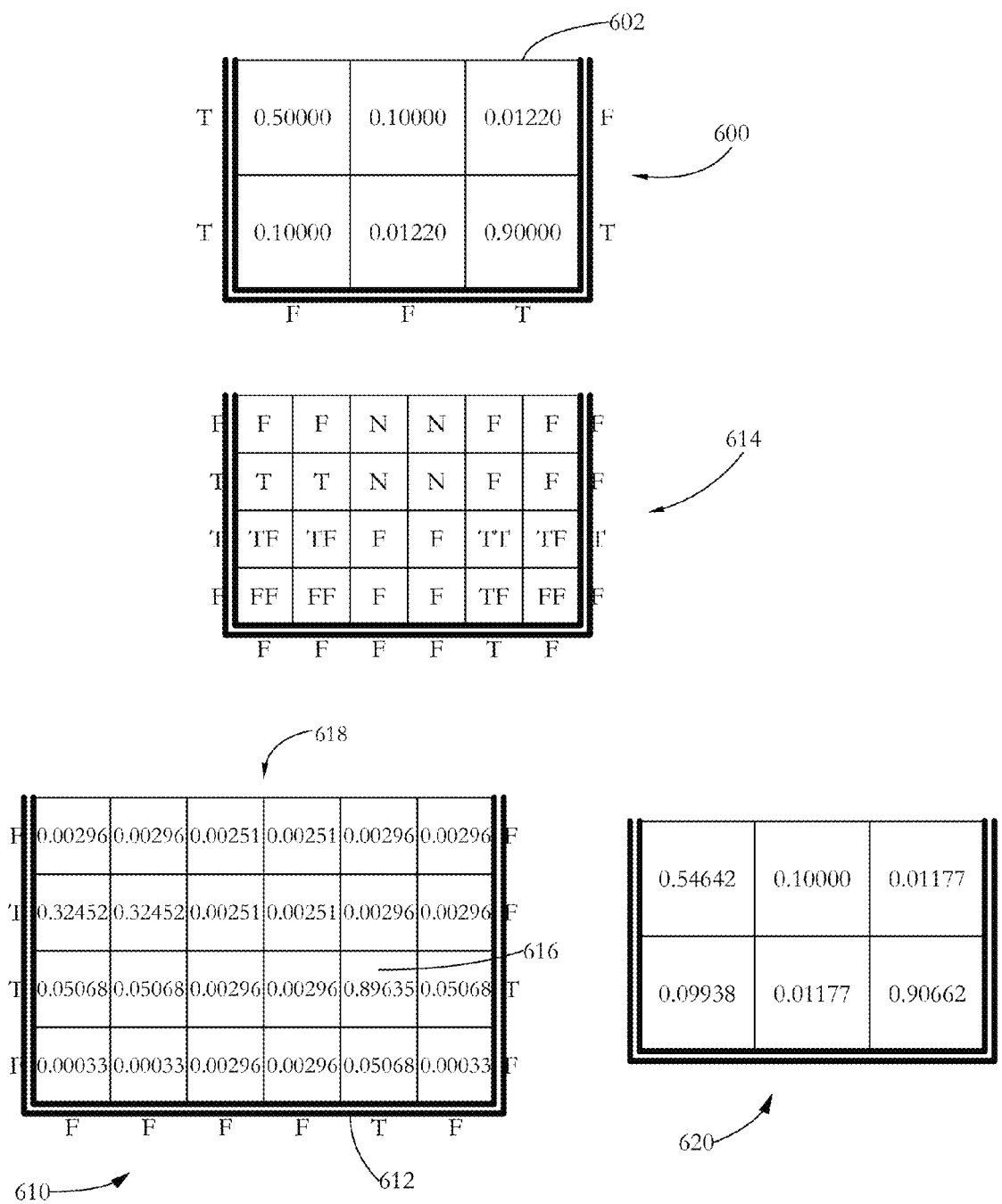
FIG. 25 shows two exemplary, simplified 2-D spatial distributions having different pixel sizes according to some embodiments of the present invention.

FIG. 25 illustrates two exemplary simplified maps (2-D spatial distributions) 600, 610 with different resolutions, according to some embodiments of the present invention. Map 610 has four times the pixels and twice the number of evidence points as map 600. Map 600 is bounded by a U-shaped measurement path 602. Plume detection Boolean values (True/False) at each location along the measurement path are shown on the outside of path 602. For simplicity, the wind is taken to always blow toward measurement path 602, and the detection distance is one pixel, i.e. the True/False values only apply to the adjacent pixel. The prior is taken to be a uniform 0.1, i.e. indicating a prior 10% chance of a source in each pixel. The values shown in FIG. 25 inside each pixel of map 600 represent the result of a Bayesian update performed as follows: for a T, $p(T_j|S_{xy}) = 9p(T_j|\overline{S_{xy}})$, and for a F, $p(F_j|S_{xy}) = \frac{1}{9}p(F_j|\overline{S_{xy}})$.

Similarly, map 610 is bounded by a U-shaped measurement path 612, and plume detection Boolean values at each location are shown on the outside of path 612. A matrix 604 illustrates the treatment of the corner pixels, for which two T/F values are measured. The T and F evidence have been distributed consistently with map 600, but note that we took each T in map 600 and turned it into a T and an F in map 610. We could also have turned each T into two Ts with the same ratio between the probabilities, but that would not have highlighted the localization capability as clearly. Each individual T now applies to half the area, and thus we use $p(T_j|S_{xy}) = 18p(T_j|\overline{S_{xy}})$ so that the results are directly comparable to those of map 600. Note the high probability in a pixel 616 corresponding to two T observations. In the center pixels 618 the prior is now about ¼th of the original prior, because the 4 pixels are OR-ed together. A map 620 illustrates the results of combining (OR-ing) the pixel values of map 610. The resulting probabilities are similar, though not identical, to those of the original map 600. Since in this model there can be as many sources as there are pixels, a high pixel density map can have more sources.

Multiple Wind Directions

In the example illustrated in FIG. 25, there was just one wind direction corresponding to each piece of evidence. In general, however, each piece of evidence may correspond to multiple wind directions. Consider first a wind field that is frozen in time. If we assume that a source located at each pixel produces a single plume that moves in a specific direction, we may extend the possible hypotheses at a given pixel to be the hypothesis that there is a source in each possible direction and the hypothesis that there is no source at this location.

Consider the notation $\alpha$ to refer to a range of angles $\Delta\alpha = 2\pi/N$, where N is the number of angular bins. Then the probability corresponding to $\alpha$ can we written as $$\rho'_{xy\alpha} = \frac{p(E_j | S_{xy\alpha})\rho_{xy\alpha}}{p(E_j) = \sum_{\beta} p(E_j | S_{xy\beta})\rho_{xy\beta} + p(E_j | \overline{S_{xy}})\eta_{xy}} \quad [8]$$

where the probability of there being no source is $\eta_{xy} = 1 - \Sigma\rho_{xy\alpha}$. For each step, the prior probability is distributed over the N possible angle bins $\rho_{xy\alpha} = \rho_{xy}/N$. The probability can be distributed evenly, which assumes no knowledge of the wind direction, or according to the distribution of measured wind directions. Distributing the probability according to the distribution of measured wind directions means that wind angle enters into the picture in two ways: both in the distribution of the prior among the angular bins, and in the probability kernel that determines the effect of the evidence for the different wind angles. Of all these possibilities, the angles of interest are those subtended by the vectors connecting the measurement segment and the pixel $A_{xy}$. The evidence does not affect any of the other hypotheses, so all of their probabilities remain the same. Thus, T evidence will drive the probability toward 1 for the bin connecting the evidence to the pixel, while other pixels will be driven to zero (as will $\eta_{xy}$). Conversely, F evidence will drive the bin connecting the evidence to the pixel toward zero and all the other bins toward 1. The other angular bins will also be driven toward 1, which means that to drive the overall probably quickly toward zero, it is necessary to drive a path that subtends all the angles of the wind distribution. For each new step, the new wind field distribution is applied while maintaining the angular structure caused by earlier evidence as, for example, by applying the ratio mask $$R = \frac{P_{new}(\alpha)}{P_{old}(\alpha)}.$$

This is the situation for an essentially frozen wind field, which is true for single transects in the vicinity of a pixel. For a wind field that is completely randomized from step to step on the path s, one could completely redistribute the probability among the different angular bins according to the new wind distribution, without preserving the structure created by earlier measurements. This tends to reduce the effect of F evidence, meaning that areas are cleared more slowly. A compromise between a completely frozen and completely random wind field is a slowly healing distribution that returns to a flat distribution. Such healing may be performed by angular diffusion, in which mixing between nearby angles for large probability gradients occurs more quickly than when the gradients are small. Such healing may also be performed by redistributing a portion of the angular probability evenly among all the angular bins, for example with an exponential time constant of about 0.1-1 minutes. Such healing would allow the static wind field approximation to be valid within a given transect that takes a few seconds, but later transects would start from scratch as far as the wind field is concerned.

General Discussion

The concept of expanding measurements collected in one dimension to retrieve 2-D information is a form of tomography, in which the transformation of the 2-D information into 1-D measurements occurs via an ever-changing atmospheric transport model. Consider a data stream comprising a position of a mobile platform as a function of time, $\vec{x}(t)$, the concentration of gas, c(t), the wind speed and direction $\vec{u}(t)$, and auxilliary information, e.g., atmospheric stability, photographic imagery, etc., which we shall denote collectively $S(\vec{x}, t)$. From our measurements, we would like to deduce unknown properties of any gas sources present. In particular, we would like to assess the conditional probability of the parameters describing a hypothesis given a set of observations. We can do this by choosing a functional form for hypotheses with parameters corresponding to the properties we are interested in, and then assessing the relative likelihood of each hypothesis in light of a set of observations in the context of a statistical model.

Depending on the properties of the ground (such as permeability), gas leaks originating from an underground pipe can emerge at a localized point such as hole in the pavement, or can diffuse out of the ground over an extended area. Furthermore, the total flux emerging can vary in time with changes in surface permeability. Thus, we can start with a general gas source hypothesis that has an arbitrary distribution in space and time. In practice, we would not expect to have a hope of resolving a spatial extent or time dependence without an enormous number of observations, so a more practical hypothesis would be a steady point source described by a location $\vec{r}$ and flux, $\Phi$.

In order to compare the relative veracity of different hypotheses, we would like to know the likelihood that a given hypothesis H is true given a collection of observations O. The i'th observation, $\vec{O}_i$, is a vector since it may involve measuring of a number of observables. In addition to the hypotheses H between which we wish to distinguish, the conditions (such as the atmospheric stability, wind conditions, path of the vehicle, etc.) under which this observation is made may be represented by parameter vector $\vec{C}_i$.

The likelihood of hypothesis H given the observation $\vec{O}_i$ is the conditional probability density of the observation, regarded as a function of the hypothesis, i.e., $$L(H;\vec{O}_i,\vec{C}_i)=P(\vec{O}_i|H,\vec{C}_i) \quad [9]$$

If the observations are assumed to be independent, the likelihood of a given hypothesis is the product of the likelihoods for each observation:

$$\mathcal{L}(\mathcal{H};O) = \prod_i \mathcal{P}(\vec{O}_i | \mathcal{H}, \vec{C}_i) \quad [10]$$

If we already have some information that confers a relative preference to different hypotheses in the form of a prior probability density P(H), we can incorporate this knowledge according to Bayes' theorem to give a posterior probability density after the observations as:

$$\mathcal{P}(\mathcal{H}|O) \propto \prod_i \mathcal{P}(\vec{O}_i|\mathcal{H},\vec{C}_i)\mathcal{P}(\mathcal{H}) \quad [11]$$

In order to construct a probability density function $P(\vec{O}_i|H,\vec{C}_i)$ for the observation $\vec{O}_i$, we specify the observables, which are its components $O_{ij}$. Strictly, this may be a joint probability density, but it may be possible to choose the observables so that the probability density function factorizes at least approximately into a product of independent functions.

$$\mathcal{P}(\vec{O}_i|\mathcal{H},\vec{C}_i) \approx \prod_j \mathcal{P}_j(\vec{O}_{ij}|\mathcal{H},\vec{C}_i) \quad [12]$$

An appropriate model in the context of deducing gas source properties is the Pasquill-Gifford Gaussian plume model, described above. In this model, gas from a point source is assumed to propagate downwind, dispersing in the horizontal and vertical directions (y and z, respectively) according to a two-dimensional Gaussian distribution. The development of the horizontal and vertical extents ($\sigma_y$ and $\sigma_z$) of the plume as a function of time is governed by the wind speed and the degree of atmospheric turbulence, classified from "A" to "F" in order of increasing stability.

Let us define a track as the path of our mobile gas detection system along with the quantities measured as a function of time. In the context of the plume model, we generally gain the most information about a gas source location from the portion(s) of the track intersecting a plume. One step in the data analysis is to find and isolate such segments of the track. Identifying such segments can be accomplished though spatial-scale and threshold analysis. The spatial-scale analysis converts $\vec{x}(t)$ and $\vec{c}(t)$ into $\vec{c}(x)$. Let us define a positive indication as having occurred when the output of the threshold analysis shows that the measured concentration has risen above a threshold $c_T$ and has remained so for spatial extent w which satisfies $w_{min} < w_i < w_{max}$. Here, $w_{min}$ and $w_{max}$ are chosen to minimize false indications arising from statistical fluctuations at scales smaller than $w_{min}$, or from changes in the background gas concentration occurring on scales greater than $w_{max}$. In one particular implementation, the threshold analysis may be accomplished using a Gaussian kernel analysis yielding the position $\vec{x}_0$ where the maximum concentration was observed, an amplitude a, and a width w of the kernel that best match the recorded concentration curve. The amplitude may be taken to be the background-subtracted maximum detected gas concentration.

To determine the location of a potential gas emission source, consider the simplifying assumption that the source flux is constant and is emerging from a single point. The hypothesis can then be described as:

$$H=[\vec{r},\Phi] \quad [13]$$

We would like to identify observables which we believe are useful for deducing source location based on the output of a spatial-scale and threshold analysis. In particular, we may be able to restrict the position of the unknown source using our measurements of the location of the maximum concentration $\vec{x}_0$, the time at which the maximum concentration was observed, $t_0$, the wind speed and direction as recorded up to the observation of the maximum, $\vec{u}(t)$ and the observed atmospheric stability class, S.

Three parameters of particular interest are an impact parameter, a plume width, and an observed flux.

Let us define a line $\vec{l}(t)$, that traces the path of the wind backward in time from $x_0$:

$$\vec{l}(t) = \vec{x}_0 - \int_t^{t_0} \vec{u}(t')dt', \, t < t_0 \quad [14]$$

For a hypothetical source at position $\vec{r}_0$, we define $t_h$ as the point that minimizes the distance between $\vec{l}(t)$ and $\vec{r}_0$. Let b be that minimum distance, and let $l_0$ be the distance along $\vec{l}(t)$ between $\vec{x}_0$ and $\vec{l}(t_h)$. Here b is analogous to an impact parameter, and both it and $l_0$ may be calculated from the position of the indication and for each possible source location. If we characterize the distribution of b and $l_0$ for a collection of indications from known sources under different conditions, this yields $P(b, l_0 | \vec{r}, \Phi, \vec{C})$, whose marginals may then be used as a component in the likelihood for source location. Such an approach is likely to be most useful when the wind speed is strong enough, compared to the degree of turbulent diffusion, that advection is the dominant mechanism for transporting the gas from the source to the detector.

The width of the observed gas concentration peak, w, is another useful parameter for localizing a source. More specifically, if $\theta$ is the angle between the average wind direction and the direction of travel, then $$w' = w \sin\theta \quad [15]$$

reflects the actual width of the plume at $\vec{x}_0$. If the source is close to the point of observation, then w' is smaller compared to cases where the sources is more distant.

The horizontal and vertical development of the plume is governed by the atmospheric stability class, the wind speed and the variability of the wind direction. We can construct a probability density of the form $P(w'|\vec{r},\vec{C})$, where within $\vec{C}$ are included $l_0$, the downwind distance traveled by the plume, the wind statistics $\vec{u}$ and $\sigma_u$ during the time of travel $t_h < t < t_0$ and the effects of spreading due to the atmospheric stability class.

The total flux, $\phi$, of gas observed along the path of the mobile platform may be estimated to within a factor as:

$$\phi \sim a w \bar{u} \sin\theta \quad [16]$$

where $\bar{u}$ is the mean wind speed during the observation. For a given set of atmospheric conditions, we would expect $\phi$ to decrease as we move farther away from a given source because the plume has had more time to diffuse in the y and z directions. However, the observed flux is also a function of the source flux, $\Phi$. Since a given observed flux could have originated from a smaller source located near the measurement path or a large one farther away, we can write a probability density function (PDF) of the form $$P(\phi,w'|l_0,t_0-t_h) = \int P(\phi,w'|\Phi,l_0,t_0-t_h)P(\Phi)d\Phi \quad [17]$$

In some embodiments, the probability density functions describing the functions $P_j$ of Eq. [12] can be determined empirically by experiments conducted with known sources with known properties. The functions $P_j$ may be functions of many variables. The dependence on some of those variables may be difficult to determine empirically, since collecting enough data when one cannot control all of the parameters is sometimes a challenge. In such cases it might suffice to assert a functional form for the dependence on a particular parameter on plausible theoretical grounds.

Given the complexity of atmospheric transport phenomena, especially for plumes propagating near the ground on short time and distance scales, some observables are likely to provide more information or be more powerful for determining the unknown source properties. In some embodiments, the relative importance of one observable compared to another may be changed as a function of weather conditions or other circumstances. Furthermore, some observations might be of higher quality or provide more information than others. The structure of the probability density functions themselves may account for different informational content of different observations. In some embodiments, the relative importance of each observable for the ith observation is weighted as follows.

In the normal application of Bayes' theorem, if we regard the observables of $\vec{O}_i$ of the ith observation as being independent, the change in our state of knowledge as a result of the i'th observation is $$P(H|O_i, \ldots, O_1, C_i, \ldots, C_1) \propto P(O_{i1}, \ldots, O_{in}|H_iC_i) P$$
$$(H|O_{i-1}, \ldots, O_1, C_{i-1}, \ldots, C_1) \propto P(O_{i1}|H_iC_i) \ldots$$
$$P(O_{in}|H_iC_i) P(H|O_{i-1}, \ldots, O_1, C_{i-1}, \ldots C_1) \quad [18]$$

We may empirically introduce weights $w_1, \ldots, w_n$ (which may depend on $C_i$) to emphasize or deemphasize the effects of the individual factors, so that we consider instead a likelihood of the form $$P(O_{i1}|H,C_i)^{w_1} \ldots P(O_{in}|H,C_i)^{w_n} \quad [19]$$

If we work in terms of the log likelihoods, these weights act as coefficients of the linear combination of the log likelihoods of the individual observables within the observation. It is similarly possible to introduce weighting factors to change the relative importance of the observations as well as of the observables within an observation.

In some embodiments, one evaluated quantity of particular interest is the degree of belief in a given hypothesis with respect to another. Suppose we have collected a number of observations and have computed L(O|H) using a likelihood function suitable for localizing gas sources. Let us further suppose that the joint likelihood indicates two equally likely locations for the source of the leak. One of the locations is in a corn field and the other is near the road where there are underground gas distribution lines. Even though the determined likelihood of both locations may be equal, our degree of belief is higher for the hypothesis that the leak is located near the gas distribution line.

Bayes' theorem allows us calculate such a degree of belief by combining the likelihoods generated using the observations with any prior information we already have about possible or probable leaks. For example, we can use a map of the gas distribution system, and if we are willing to make the assumption that leaks from the system do not travel far from the system's pipes before emerging above ground, we could represent this prior knowledge as a function $P(\bar{r})$ which has a large value at coordinates near the pipeline and that is small (or zero) elsewhere. In some embodiments, we may also place constraints on fluxes of leaks that may be present, and encapsulate them in a function $P(\Phi)$. These priors represent our initial state of knowledge before any observations are made, and Bayes' theorem gives us a consistent way of modifying this state of belief as a result of making observations.

CONCLUSION

The exemplary systems and methods described above allow a surveyor to locate potential gas leak sources efficiently and effectively in highly populated areas, and allow the use of data from multiple measurement runs to generate a 2-D spatial distribution (map) of desired parameter values.

It will be clear to one skilled in the art that the above embodiments may be altered in many ways without departing from the scope of the invention. For example, gas leaks may include, but are not limited to: leaks from gas pipes or transportation systems (e.g., natural gas leaks), leaks from gas processing or handling facilities, and emissions from gas sources into the environment (e.g., pollution, gas emission from landfills, etc.). Gas concentration measurements are preferably performed rapidly (e.g., at a rate of 0.2 Hz or greater, more preferably 1 Hz or greater). This enables the concept of driving a vehicle at normal surface street speeds (e.g., 35 miles per hour) while accumulating useful gas concentration and wind measurement data. However, embodiments of the invention do not depend critically on the gas detection technology employed. Any gas concentration measurement technique capable of providing gas concentration measurements can be employed in some embodiments.

Although the gas concentration measurements are preferably performed while the gas measurement device is moving, at least some gas concentration measurements can be performed while the gas concentration measurement device is stationary. Such stationary gas concentration measurements may be useful for checking background gas concentrations, for example. While real-time measurements are preferred, post analysis of more sparsely sampled data, e.g., via vacuum flask sampling and later analysis via gas chromatography or other methods, may be used in some embodiments. Optionally, measurements can be made on different sides of the road or in different lanes to provide more precise localization of the leak source. Optionally, the present approaches can be used in conjunction with other conventional methods, such as visual inspection and/or measurements with handheld meters to detect emitted constituents, to further refine the results. Optionally, measurements can be made at reduced speed, or with the vehicle parked near the source, to provide additional information on location and/or source attribution.

Optionally, the system can include a source of atmospheric meteorological information, especially wind direction, but also wind speed or atmospheric stability conditions, either on-board the vehicle or at a nearby location. The stability of the atmospheric conditions can be estimated simply from the wind speed, the time of day, and the degree of cloudiness, all of which are parameters that are available either on the vehicle or from public weather databases. Optionally, the computer system can include an on-board video camera and logging system that can be used to reject potential sources on the basis of the local imagery collected along with the gas concentration and wind data. For example, a measured emissions spike could be discounted if a vehicle powered by natural gas passed nearby during the measurements. Optionally, repeated measurements of a single location can be made to provide further confirmation (or rejection) of potential leaks. Accordingly, the scope of the invention should be determined by the following claims and their legal equivalents.

It will be clear to one skilled in the art that the above embodiments may be altered in many ways without departing from the scope of the invention. Accordingly, the scope of the invention should be determined by the following claims and their legal equivalents.

What is claimed is:

1. A non-transitory computer-readable medium encoding instructions which, when executed by a computer system comprising at least one processor, cause the at least one processor to:
   identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run; and
   update the prior 2-D surveyed area to generate a posterior 2-D surveyed area according to a second set of gas emission survey data resulting from a second mobile measurement run, the second set of gas emission survey data comprising a second set of associated atmospheric condition data characterizing the second mobile measurement run, wherein updating the prior 2-D surveyed area comprises determining a posterior probability of missing detection of a potential gas source situated at a given location according to: i. a prior probability of missing detection of the potential gas source situated at the given location after the first mobile measurement run, and ii. a probability of missing detection of the potential gas source situated at the given location during the second mobile measurement run.

2. A computer system comprising at least one processor configured to:
identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run; and
update the prior 2-D surveyed area to generate a posterior 2-D surveyed area according to a second set of gas emission survey data resulting from a second mobile measurement run, the second set of gas emission survey data comprising a second set of associated atmospheric condition data characterizing the second mobile measurement run, wherein updating the prior 2-D surveyed area comprises determining a posterior probability of missing detection of a potential gas source situated at a given location according to: i. a prior probability of missing detection of the potential gas source situated at the given location after the first mobile measurement run, and ii. a probability of missing detection of the potential gas source situated at the given location during the second mobile measurement run.

3. A non-transitory computer-readable medium encoding instructions which, when executed by a computer system comprising at least one processor, cause the at least one processor to:
identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during first mobile measurement run would satisfy a probability condition; and
update the prior 2-D surveyed area to generate a posterior 2-D surveyed area according to a second set of gas emission survey data resulting from a second mobile measurement run, wherein updating the prior 2-D surveyed area comprises determining a posterior probability of missing detection of a potential gas source situated at a given location according to a product of: i. a prior probability of missing detection of the potential gas source situated at the given location after the first mobile measurement run, and ii. a probability of missing detection of the potential gas source situated at the given location during the second mobile measurement run.

4. A computer system comprising at least one processor configured to:
identify a prior 2-D surveyed area according to a first set of gas emission survey data resulting from a first mobile measurement run performed by a mobile measurement device along a first measurement path, the first set of gas emission survey data comprising a trajectory of the first measurement path and a first set of associated atmospheric condition data characterizing the first mobile measurement run, the prior 2-D surveyed area being an area having a boundary determined such that if a potential gas emission source were located in the prior 2-D surveyed area and had a rate of emission meeting a minimum emission rate condition, then an estimated prior probability of detection of the potential gas emission source according to gas concentration data acquired during first mobile measurement run would satisfy a probability condition; and
update the prior 2-D surveyed area to generate a posterior 2-D surveyed area according to a second set of gas emission survey data resulting from a second mobile measurement run, wherein updating the prior 2-D surveyed area comprises determining a posterior probability of missing detection of a potential gas source situated at a given location according to a product of: i. a prior probability of missing detection of the potential gas source situated at the given location after the first mobile measurement run, and ii. a probability of missing detection of the potential gas source situated at the given location during the second mobile measurement run.

5. A non-transitory computer-readable medium encoding instructions which, when executed by a computer system comprising at least one processor, cause the at least one processor to:
receive a prior 2-D surveyed area; and
update the prior 2-D surveyed area to generate a posterior 2-D surveyed area according to a set of gas emission survey data resulting from a mobile measurement run performed by a mobile measurement device along a measurement path, the set of gas emission survey data reflecting a trajectory of the measurement path and a set of associated atmospheric condition data characterizing the mobile measurement run, wherein the posterior 2-D surveyed area is an area having a boundary such that if a potential gas emission source were located in the posterior 2-D surveyed area and had a rate of emission meeting a minimum emission rate condition, then an estimated posterior probability of detection of the potential gas emission source according to gas concentration data acquired during the mobile measurement run would satisfy a probability condition, and wherein updating the prior 2-D surveyed area comprises determining the posterior probability of missing detection of a potential gas source situated at a given location according to a product of: i. a prior probability, defined by the prior 2-D surveyed area, of missing detection of the potential gas source situated at the given location and ii. a probability of missing detection of the potential gas source situated at the given location during the mobile measurement run.

6. The computer-readable medium of claim 1, wherein the instructions further cause the at least one processor to identify the posterior 2-D surveyed area according to an atmospheric transport model employing the second set of associated atmospheric condition data.

7. The computer-readable medium of claim 1, wherein the instructions further cause the at least one processor to generate display data for displaying a map of the posterior 2-D surveyed area to a user.

8. The computer-readable medium of claim 7, wherein the map of the posterior 2-D surveyed area comprises representations of underground gas transmission pipelines.

9. The computer-readable medium of claim 1, wherein the first set of associated atmospheric condition data comprises a plurality of wind speed and wind direction values acquired along the first measurement path.

10. The computer-readable medium of claim 1, wherein the second measurement run is performed along a second measurement path different from the first measurement path.

11. The system of claim 2, wherein the at least one processor is further configured to identify the posterior 2-D surveyed area according to an atmospheric transport model employing the second set of associated atmospheric condition data.

12. The system of claim 2, wherein the at least one processor is further configured to generate display data for displaying a map of the posterior 2-D surveyed area to a user.

13. The system of claim 12, wherein the map of the posterior 2-D surveyed area comprises representations of underground gas transmission pipelines.

14. The system of claim 2, wherein the first set of associated atmospheric condition data comprises a plurality of wind speed and wind direction values acquired along the first measurement path.

15. The system of claim 2, wherein the second measurement run is performed along a second measurement path different from the first measurement path.

16. The computer-readable medium of claim 5, wherein the instructions further cause the at least one processor to identify the posterior 2-D surveyed area according to an atmospheric transport model employing the second set of associated atmospheric condition data.

17. The computer-readable medium of claim 5, wherein the instructions further cause the at least one processor to generate display data for displaying a map of the posterior 2-D surveyed area to a user.

18. The computer-readable medium of claim 17, wherein the map of the posterior 2-D surveyed area comprises representations of underground gas transmission pipelines.

19. The computer-readable medium of claim 5, wherein the first set of associated atmospheric condition data comprises a plurality of wind speed and wind direction values acquired along the first measurement path.

20. The computer-readable medium of claim 5, wherein the second measurement run is performed along a second measurement path different from the first measurement path.

* * * * *